United States Patent
Prasad et al.

(10) Patent No.: US 10,006,882 B2
(45) Date of Patent: Jun. 26, 2018

(54) BIOSENSING SYSTEM AND METHODS USING ELECTRON-IONIC MECHANISMS AT FLUID-SENSOR INTERFACES

(71) Applicant: EnLiSense, LLC, Allen, TX (US)

(72) Inventors: Shalini Prasad, Allen, TX (US);
Sriram Muthukumar, Allen, TX (US);
Anjan Panneer Selvam, Richardson, TX (US)

(73) Assignee: EnLiSense, LLC, Allen, TX (US)

( * ) Notice: Subject to any disclaimer, the term of this patent is extended or adjusted under 35 U.S.C. 154(b) by 119 days.

(21) Appl. No.: 14/946,899

(22) Filed: Nov. 20, 2015

(65) Prior Publication Data

US 2016/0146754 A1    May 26, 2016

Related U.S. Application Data

(60) Provisional application No. 62/082,979, filed on Nov. 21, 2014.

(51) Int. Cl.
  *G01N 27/447* (2006.01)
  *G01N 33/543* (2006.01)
  (Continued)

(52) U.S. Cl.
  CPC ......... *G01N 27/447* (2013.01); *A61B 5/1468* (2013.01); *A61B 5/1477* (2013.01);
  (Continued)

(58) Field of Classification Search
  CPC ..................... G01N 27/447–27/44795; G01N 27/327–27/3278
  (Continued)

(56) References Cited

U.S. PATENT DOCUMENTS 4,334,880 A   6/1982  Malmros et al.
5,624,537 A   4/1997  Turner et al.
(Continued)

OTHER PUBLICATIONS

Makarova, et al, "Selective Absorption of Thiol Molecules at Sulfur Vacancies on MoS$_2$(0001), Followed by Vacancy Repair via S-C Dissociation," J. Phys. Chem. C 2012, 116, Oct. 2, 2012, pp. 22411-22416.
(Continued)

*Primary Examiner* — Bach T Dinh
(74) *Attorney, Agent, or Firm* — Alliance IP, LLC

(57) ABSTRACT

An example biosensor is provided and includes a semiconductor sensing element, a first electrode and a second electrode located on a first plane of the sensing element with a first electric field being applied thereacross, a third electrode located on a second plane of the sensing element parallel to and removed from the first plane with a second electric field being applied across the first electrode and the third electrode perpendicular to the first electric field, and a dielectric substrate having a first portion that constrains a fluid including an analyte on a surface of the sensing element, and a second portion that facilitates dielectric separation of the fluid from the electrodes. The mutually perpendicular electric fields facilitate adjusting a height of a fluid-sensor interface comprising an electrical double layer in the fluid enabling detection and characterization of the analyte.

16 Claims, 14 Drawing Sheets

(51) Int. Cl.
*A61B 5/1477* (2006.01)
*A61B 5/1468* (2006.01)

(52) U.S. Cl.
CPC .... *G01N 33/5438* (2013.01); *A61B 2562/028* (2013.01); *A61B 2562/12* (2013.01)

(58) Field of Classification Search
USPC ............... 204/450–470, 546–550, 600–621, 204/643–645, 403.01–403.15; 205/777.5–778, 792
See application file for complete search history.

(56) References Cited

U.S. PATENT DOCUMENTS

| | | |
|---|---|---|
| 6,251,691 B1 | 6/2001 | Seul |
| 2003/0146100 A1 | 8/2003 | Huang et al. |
| 2005/0113657 A1 | 5/2005 | Alarcon et al. |
| 2006/0204428 A1 | 9/2006 | Noy et al. |
| 2007/0295988 A1* | 12/2007 | Yamamoto ......... G01N 27/4145 257/147 |
| 2011/0263036 A1* | 10/2011 | Blauw ................ G01N 27/4148 436/149 |
| 2012/0156688 A1* | 6/2012 | McAlpine .............. B82Y 15/00 435/7.1 |
| 2013/0244154 A1* | 9/2013 | Yamamoto ......... G03G 9/08755 430/105 |
| 2013/0248380 A1 | 9/2013 | Cui et al. |
| 2014/0252421 A1* | 9/2014 | Liu ................... H01L 29/66477 257/253 |
| 2014/0353171 A1* | 12/2014 | Wilson ................. B01L 3/5088 205/777.5 |

OTHER PUBLICATIONS

Chua et al, "Monothiolation and Reduction of Graphene Oxide via One-Pot Synthesis: Hybride Catalyst for Oxygen Reduction," ACS Nano, vol. 9, No. 4, Mar. 27, 2015, pp. 4193-4199.

Mattson, et al., "A Practical Approach to Crosslinking," Molecular Biology Reprts 17:, pp. 167-183, 1993.

Armbruster, et al., "Limit of Blank, Limit of Detection and Limit of Quantitation," Clin Biochem Rev., vol. 29, Suppl (i), Aug. 2008, pp. S49-S52.

Velev, et al, "Particle-localized AC and DC Manipulation and Electrokinetics," Annu. Rep. Prog. Chem., Sect. C, 2009, 105, pp. 213-246.

* cited by examiner

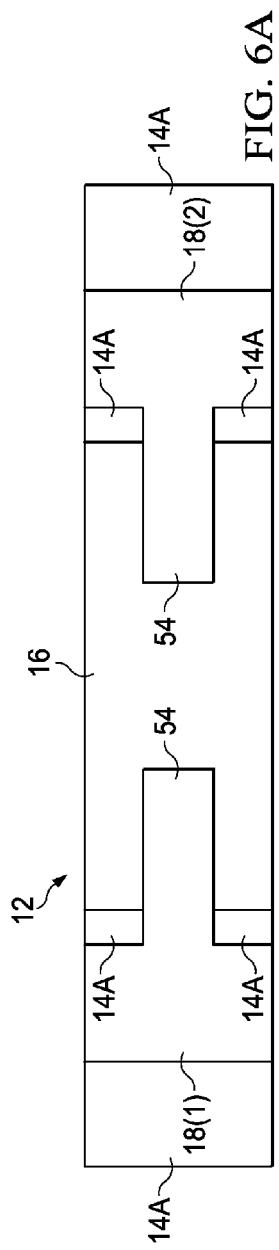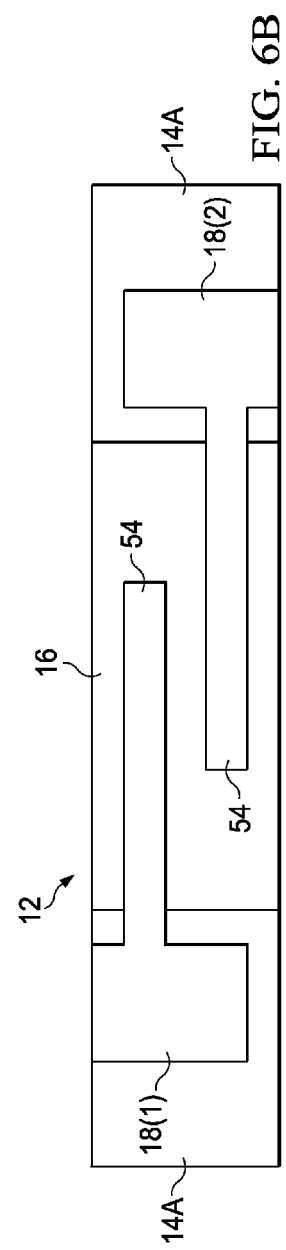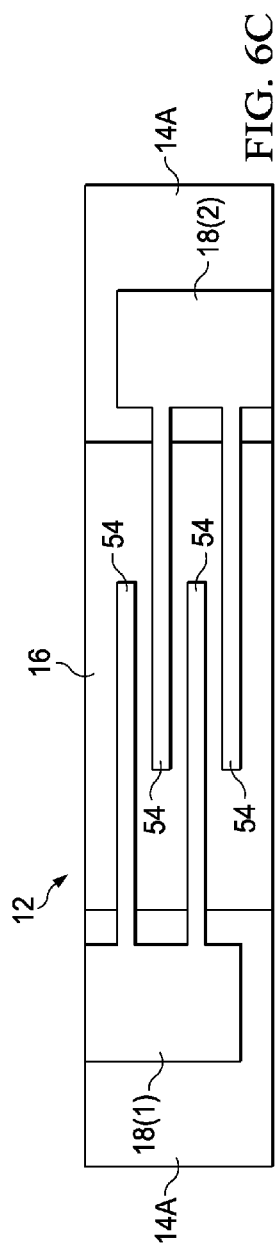

| O | (T1.T2)(O.B) | (T1.T2)(O.B') | B | OUTPUT | BINDING | LED/DIGITAL OUTPUT |
|---|---|---|---|---|---|---|
| 1 | 0 | 1 | 0 | N/A | ERROR | N/A |
| 1 | 0 | 1 | 1 | (T1.T2)(O.B') | NON-SPECIFIC/NOISE | OFF |
| 1 | 1 | 0 | 0 | N/A | ERROR | N/A |
| 1 | 1 | 0 | 1 | (T1.T2)(O.B) | SPECIFIC | ON |

FIG. 11  TRUTH TABLE FOR 2-TO-1 MULTIPLEXER

BIOSENSING SYSTEM AND METHODS USING ELECTRON-IONIC MECHANISMS AT FLUID-SENSOR INTERFACES

CROSS-REFERENCE TO RELATED APPLICATION

This application claims the benefit of priority under 35 U.S.C. § 119(e) to U.S. Provisional Patent Application Ser. No. 62/082,979, filed on Nov. 21, 2014 and entitled BIOSENSING AT SEMICONDUCTOR-ELECTROLYTE INTERFACES USING ELECTRON-IONIC MECHANISMS, the disclosure of which is hereby incorporated by reference in its entirety.

TECHNICAL FIELD

This disclosure relates in general to the field of biosensing and, more particularly, to systems and methods for facilitating biosensing using electron-ionic mechanisms at fluid-sensor interfaces.

BACKGROUND

Biosensing technology is increasingly in demand for wearable and non-invasive sensors that can monitor multiple target agents, such as chemical molecules, biological molecules, enzymes, proteins, metabolites, and peptides, including multiple target agents of the same type, or multiple target agents of different types from a single sample type. Such biosensors can find use in healthcare, food testing, defense applications, environmental monitoring, or other fields where it is desirable to detect the presence or absence of a capture analyte. Biosensors may be designed to support detection of a wide range of chemical agents, and a wide range of biomarkers that are indicators of a person's physiological state (e.g., for detecting diseases and monitoring health conditions of the user).

BRIEF DESCRIPTION OF THE DRAWINGS

To provide a more complete understanding of the present disclosure and features and advantages thereof, reference is made to the following description, taken in conjunction with the accompanying figures, wherein like reference numerals represent like parts, in which:

FIG. 6A is a simplified block diagram illustrating yet other example details of embodiments of the biosensing system;

FIG. 6B is a simplified block diagram illustrating yet other example details of embodiments of the biosensing system;

FIG. 6C is a simplified block diagram illustrating yet other example details of embodiments of the biosensing system;

FIG. 11 is a simplified diagram illustrating yet other example details of embodiments of the biosensing system;

DETAILED DESCRIPTION OF EXAMPLE EMBODIMENTS

Overview

An example biosensor that facilitates biosensing using electron-ionic mechanisms at fluid-sensor interfaces is provided and includes a semiconductor sensing element, a first electrode and a second electrode located on a first plane of the sensing element with a first electric field being applied thereacross, a third electrode located on a second plane of the sensing element parallel to and removed from the first plane with a second electric field being applied across the first electrode and the third electrode perpendicular to the first electric field, and a dielectric substrate having a first portion that constrains a fluid including an analyte on a surface of the sensing element, and a second portion that facilitates dielectric separation of the fluid from the electrodes. The mutually perpendicular electric fields facilitate adjusting (e.g., tuning changing, modifying, etc.) a height of an electrical double layer in the fluid enabling detection and characterization of the analyte.

As used herein, the term "biosensor" can refer to any suitable sensor used in biochemical testing, biological testing, electrochemical testing, etc. The term "analyte" refers to a substance being identified, tested, characterized and otherwise measured; the analyte can comprise molecules of a single target species (e.g., glucose), or molecules of multiple target species (e.g., glucose and synthetic deoxyribose nucleic acid (DNA)). Examples of analyte include latex beads, lipid vesicles, whole chromosomes, cells and biomolecules including proteins and nucleic acides, gaseous molecules (e.g., ethylene), metal or semiconductor colloids and clusters, small molecules in the size range of sub-nanometer to millimeter, metabolites, and other such chemical molecules.

Example Embodiments

Figure 1A:
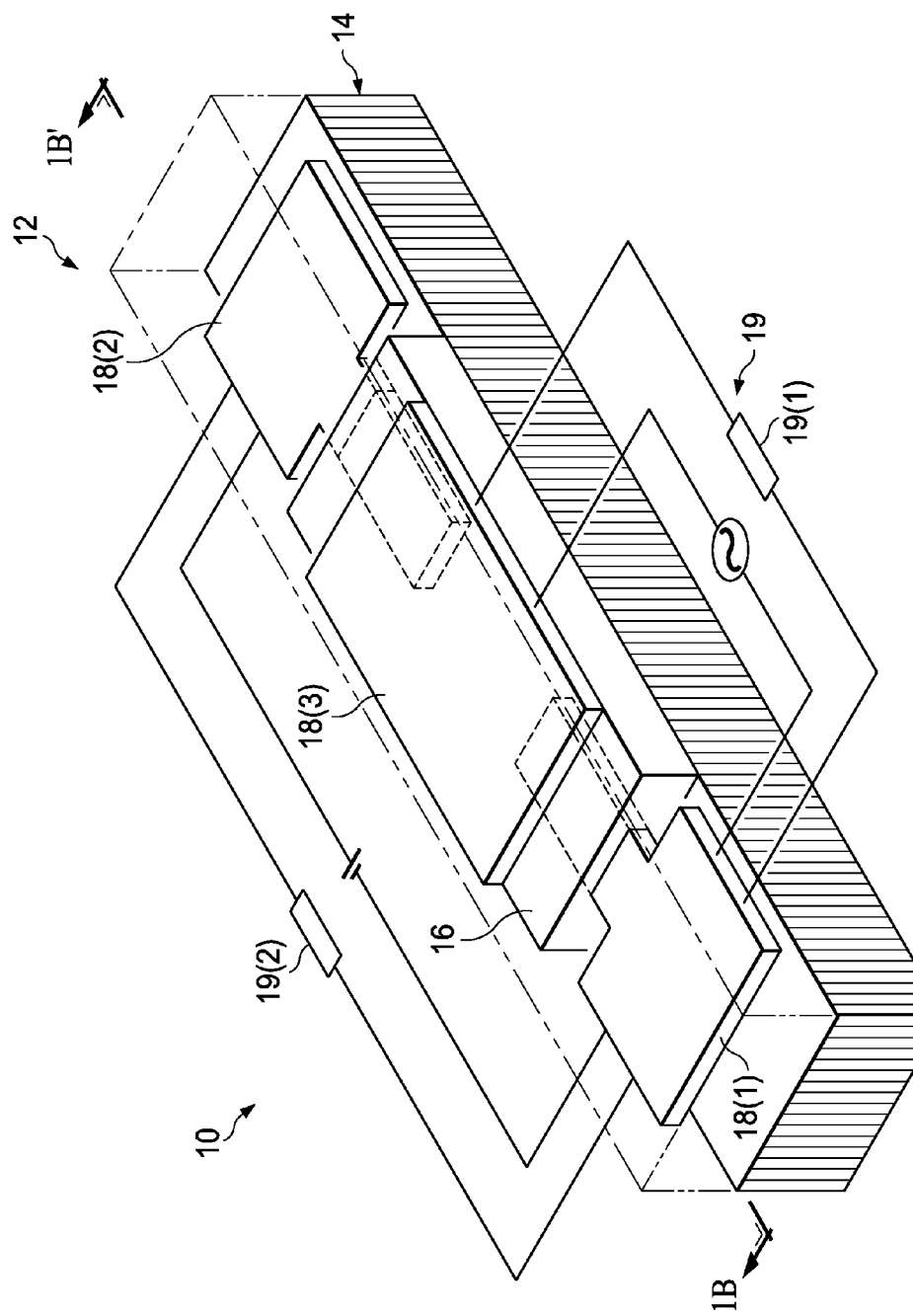
FIG. 1A is a simplified block diagram illustrating a biosensing system using electron-ionic mechanisms at fluid-sensor interfaces.
Figure 1B:
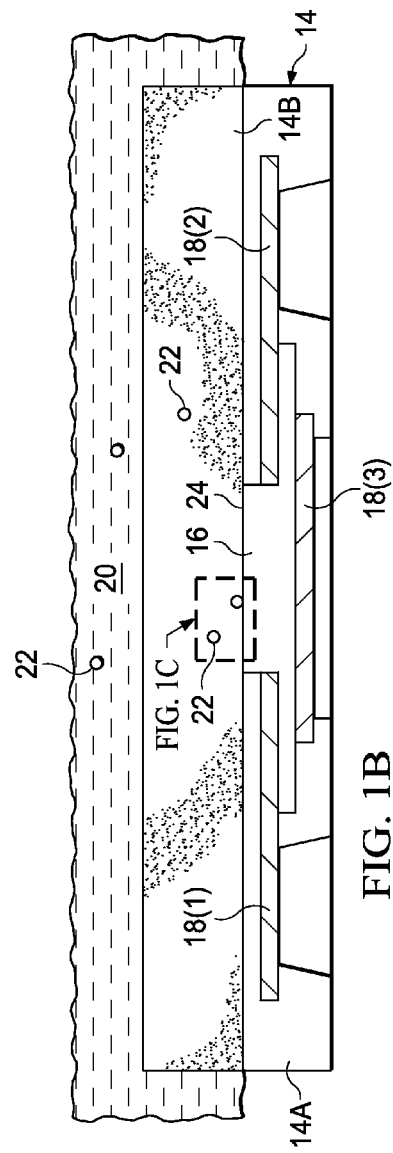
FIG. 1B is a simplified block diagram illustrating example details of embodiments of the biosensing system.
Figure 1C:
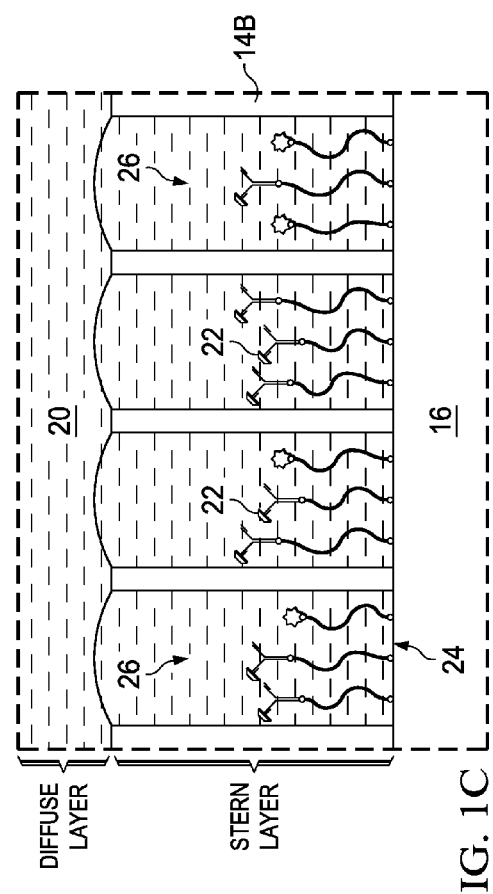
FIG. 1C is a simplified block diagram illustrating example operations and other example details of an embodiment of the biosensing system.

Turning to FIGS. 1A-1C, FIGS. 1A-1C are simplified block diagrams illustrating a biosensing system 10 for facilitating biosensing using electron-ionic mechanisms at fluid-sensor interfaces in accordance with one example embodiment; FIG. 1B is a cross-section along axis B-B'; and FIG. 1C is an example detail of the cross-section. FIG. 1A illustrates a biosensing system 10 comprising a biosensor 12 including a substrate 14, a sensing element 16, a plurality of electrodes 18(1)-18(3), and an output 19 comprised of two components, baseline 19(1) and response 19(2).

A transverse voltage may be applied across some of electrodes 18 (e.g., 18(1) and 18(2)); an orthogonal voltage may be applied across other electrodes 18 (e.g., 18(1) and 18(3)). Electrodes 18 (e.g., 18(1) and 18(2)) across which the transverse voltage is applied may be referred to as 'transverse electrode;' electrodes 18 (e.g., 18(1) and 18(3)) across which the orthogonal voltage is applied may be referred to as 'orthogonal electrodes.' In a general sense, 'transverse' and 'orthogonal' refer to direction of electric fields produced by the respective voltages; in various embodiments, the electric field produced by the transverse voltage is perpendicular to the electric field produced by the orthogonal voltage. In some embodiments, the transverse voltage may comprise direct current (DC) voltage and the orthogonal voltage may comprise alternating current (AC) voltage. In other embodiments, the transverse voltage may comprise AC voltage, and the orthogonal voltage may comprise DC voltage. In yet other embodiments, the transverse voltage may initially comprise AC voltage, which may be switched to DC voltage, and the orthogonal voltage may comprise AC voltage.

Baseline 19(1) comprises impedance, or capacitance, or current measured across orthogonal electrodes 18(1) and 18(3) and establishes a baseline value for the respective measurement; response 19(2) comprises impedance, or capacitance, or current measured across transverse electrodes 18(1) and 18(2). In various embodiments, comparison between baseline 19(1) and response 19(2) can indicate a signal-to-noise ratio (SNR) of the measurements and provide detection and/or measurement of concentration of an analyte 22 in a fluid 20.

Substrate 14 generally allows for fluid containment such that a portion of fluid 20 comprising analyte 22 is in contact with sensing element 16 at a fluid-sensor interface 24, as indicated in FIG. 1B. Note that fluid containment is in three dimensions, for example, both vertically and laterally (e.g., perpendicular and parallel to sensing element surface.) Fluid-sensor interface 24 comprises a zone of interaction between sensing element 16 and fluid 20. In some embodiments, fluid-sensor interface 24 comprises a surface of sensing element 16 in contact with fluid 20; in other embodiments, fluid-sensor interface 24 comprises an additional layer of linker molecules that are bound to the surface of sensing element 16; in yet other embodiments, fluid-sensor interface 24 comprises an additional layer of capture probes that bind to the linker molecules. In yet other embodiments, fluid-sensor interface 24 additionally comprises a layer of fluid 20 including an electrical double layer (EDL).

In some embodiments, as indicated in FIG. 1B, substrate 14 may comprise two separate portions, indicated as 14A and 14B. In an example embodiment, portion 14A comprises a hydrophobic biocompatible material (e.g., Parylene™) and portion 14B comprises a porous biocompatible hydrophilic membrane (e.g., polyimide, polyamide, nylon, alumina, polycarbonate, polymer, ceramic, etc.). In various embodiments, portion 14A may prevent direct interaction between fluid 20 and electrodes 18(1)-18(3), for example, providing dielectric separation (e.g., electrical isolation) of electrodes 18(1)-18(3) from fluid 20. In some embodiments, portion 14B may provide a fluid containment zone allowing analyte 22 of fluid 20 to bind to sensing element 16 at fluid-sensor interface 24.

Some of electrodes 18(1)-18(3) (e.g., 18(1) and 18(2)) may be located on one plane, and the other electrodes (e.g., 18(3)) may be located on another, different plane. In an example embodiment, transverse electrodes 18(1) and 18(2) may be located on a first plane of sensing element 16 and orthogonal electrode 18(3) may be located on a second plane of sensing element 16 parallel to and removed from the first plane.

To explain the fluid containment in more detail, as indicated in FIG. 1C, portion 14B may comprise pores 26 that provide a fluid containment zone allowing analyte 22 to bind to sensing element 16 at fluid-sensor interface 24 in the presence of an electric field. In some embodiments, pores 26 may comprise nanopores (e.g., diameter or size in the order of nanometers). In various embodiments, the electric field produced by the orthogonal voltage causes reversible aggregation of analyte 22 in fluid 20 into planar aggregates adjacent to fluid-sensor interface 24. The planar aggregation disassembles when the electric field is removed. In confined geometries, as in pores 26, the surface charge distribution on sensing element 16 and topography of bounding electrodes 18(1) and 18(2) may determine a nature of electron-ion interaction at fluid-sensor interface 24. The planar aggregation can include organization similar to self-assembly producing partial coverage, monolayer coverage or stretched coverage.

In various embodiments, fluid 20 wicks through pores 26 to make contact with sensing element 16 at fluid-sensor interface 24. In a general sense, when sensing element 16 having surface charge is immersed in fluid 20 containing ions, a diffuse ion cloud, called the "stern layer" forms in fluid 20 to screen (e.g., neutralize) sensing element 16's surface charge. Beyond the stern layer is a diffuse layer comprising ions providing an electrical gradient within fluid 20. The arrangement of a layer of (immobile) charges in the stern layer and the screening cloud of (mobile) counter-ions in the diffuse layer of fluid 20 is referred to as the electrical double layer (EDL). As noted previously, fluid-sensor interface 24 comprises the EDL. In the EDL of small but finite thickness, fluid 20 is not electroneutral. Consequently, electric fields acting on the EDL will set in motion ions in the diffuse layer, and these will in turn entrain surrounding fluid 20. The resulting flow fields reflect the spatial distribution of ionic current in fluid 20.

The diffuse layer may be polarized by the orthogonal electric field (i.e., the electric field produced by the orthogonal voltage) to effect charge perturbation associated with detection of target species of analyte 22 in fluid 20. The effective ionic content of the combination of the stern layer and the diffuse layer acts as a screen (e.g., charge screening) preventing the target species of analyte 22 from travelling to and binding to sensing element 16. However, excluded volume effect (e.g., 'excluded volume' of a molecule is the volume that is inaccessible to other molecules in the system as a result of the presence of the molecule) and macromolecular crowding from non-specific target species in the confined spaces (e.g., pores 26) can minimize such charge screening. Embodiments of biosensing system 10 can facilitate multiple target species detection in varying fluids; analyte 22 may comprise target species with no charge, high charge or low charge and fluid 20 may have with varying polarity levels within the broad scope of the embodiments.

For purposes of illustrating the techniques of biosensing system 10, it is important to understand the communications that may be traversing the system shown in FIG. 1. The following foundational information may be viewed as a basis from which the present disclosure may be properly explained. Such information is offered earnestly for purposes of explanation only and, accordingly, should not be construed in any way to limit the broad scope of the present disclosure and its potential applications.

Various approaches to frequent and/or continuous biosensing tend to fall into two general categories: "non-invasive" and "minimally invasive." Non-invasive monitoring determines analyte (e.g., a substance whose chemical constituents are being identified and measured) levels by directly tracking spectroscopic changes in skin and tissue. Infrared radiation and radio wave impedance spectroscopy are examples of this technology. Progress with these approaches has been slow for various reasons, such as need for frequent calibration, reproducible sample illumination, and variances in spectroscopic backgrounds between individuals. The "minimally invasive" approach avoids direct extraction of biological fluids from the body and relies on monitoring of signal changes in the biological fluids using an intermediate sensing element. Biosensors of this type typically provide specific quantitative or semi-quantitative analytical information using a biological recognition element in combination with a transducing (e.g., detecting) element.

In a general sense, typical modalities for biochemical sensing of minimally invasive biosensors utilize affinity reactions and binding as a means to transduce (e.g., convert, change, alter, etc.) the chemical sensing into optical, electrical, or mechanical signal or a combination thereof (the basic principle being predicated on binding between components of a reaction pair (e.g. antigen/antibody, hapten/antibody, etc.) where, in some cases, one component is labeled so as to be easily analyzed by some external means). Examples of specific binding substances that have been historically targeted using biosensors include antibodies, antigens, enzymes, enzyme substrates, enzyme substrate analogs, agglutinins, lectins, enzyme cofactors, enzyme inhibitors and hormones.

For example, typical biosensors utilize at least one of three different bio-sensing modalities: (1) electrical biosensors, (2) optical biosensors, and (3) mechanical biosensors. The input to such biosensors are biological molecules (e.g., molecules from biological sources, such as animals and plants). In electrical biosensors, the transduction (e.g., conversion or conveyance of energy in one form from a donor to another form at a receptor) is biochemical to electrical; in optical biosensors, the transduction is biochemical to optical to electrical; and in mechanical biosensors, the transduction is biochemical to mechanical to electrical. The measurable outputs in electrical biosensors include current, voltage and/or impedance; the outputs in optical biosensors include light intensity, and refractive index; the outputs in mechanical biosensors include resonance frequency and mass.

In an example biosensor that senses glucose concentration, an optical conduit, such as an optical fiber has an optical system at a proximal end of the optical conduit and a sensing element attached to a distal end. The sensing element includes a binding protein that binds with a target analyte, and a reporter group that undergoes a luminescence change with changing analyte concentrations. In another example, a graphene electrode is linked to a biosensing element, which is bonded to a flexible substrate. The graphene electrode has a positive terminal end and a negative terminal end; an electrical voltage is applied to the positive and negative terminals to measure an electrical current response in proportion to a lactate concentration on the biosensing element.

In yet another example, the biosensor includes a nanotube, with a lipid bilayer around the nanotube, and a sensing element connected to the lipid bilayer, the biosensor capable of detecting variations in ion transport through a protein pore. The biosensor further includes a gate electrode; a source electrode; and a drain electrode, with the nanotube connected to the gate electrode, the source electrode, and the drain electrode. Yet another example biosensor includes a selectively permeable interface membrane, a porous protein-receiving matrix adjacent to the interface membrane, an indicating electrode, an inlet conduit through which fresh protein conjugate may flow to the protein-receiving matrix, and an outlet conduit through which spent protein conjugate may be removed from the protein-receiving matrix. The selectively permeable interface membrane may be used to separate biochemical, optical or other processes from the analyte. The biosensor's in situ probe provides continuous, real-time analysis by amperometric detection of hydrogen peroxide produced as a by-product of enzymatic oxidation of a substrate by its enzyme catalyst at the probe.

In yet another biosensor, electrochemical sensors employ an ion selective electrode to detect a reaction product of an enzyme that acts as a label for one component of a specific binding pair. The biosensor includes electrically semiconductive material to which an analyte specific binding substance is suitably immobilized. By placing the analyte specific binding agent in close proximity to the semiconducting material, a change in an electrical field occurs as a result of the binding reaction, which in turn effects a change in the properties of the semiconducting material that can be measured suitably.

Such currently available sensor technologies primarily perform biometric assessments, which may not be sufficient for determining cohesive response strategies. Moreover, they typically require complex setup and trained personnel for operation and analysis. Challenges in such currently existing wearable technologies include amplifying signals using reporter molecules, use of redox probes, and low signal-to-noise ratio (SNR) without use of amplifiers. In typical biosensor technologies, it may be desirable to enable wearable and non-invasive sensor technologies that allow users to rapidly evaluate their physiological status in a continuous manner. For example, wearable, non-invasive sensors that monitor chemical and biological agents without requiring constant recalibration may be desired for maintaining stasis in humans and surrounding environments.

Biosensing system 10 is configured to address these issues (among others) to offer a system and method for facilitating biosensing using electron-ionic mechanisms at fluid-sensor interfaces. Embodiments of biosensing system 10 provide for charge transfer modulation and characterization of analyte 22 at fluid-sensor interface 24 with sensing element 16. In various embodiments substrate 14 may comprise any suitable insulating material, flexible, or rigid, that can effectively contain (e.g., constrain, enclose, hold, surround, channel, encompass, enfold, ring, etc.) fluid 20. Examples for suitable materials for substrate 14 include polymers, ceramics, glass, or combination thereof.

In one example embodiment, substrate 14 comprises a flexible polymer having nano-pores that facilitate contact of fluid 20 in the nano-pores with sensing element 16. In another example embodiment, substrate 14 may comprise a porous membrane that allows for fluid 20 to wick to sensing element 16 and provides support to biosensor 12. Substrate 14 may also include a hydrophobic material, such as Prylene™, that forms an isolation barrier between wicked fluid 20 in the membrane and electrodes 18(1)-18(3). Parylene™ is an example of a hydrophobic biocompatible material that can form a non-conducting isolation barrier such that the output of biosensor 12 captures electron-ion interaction at fluid-sensor interface 24 between fluid 20 and sensing element 16, and does not capture any direct interaction of fluid 20 with electrodes 18(1)-18(3).

In various embodiments, sensing element 16 provides for binding (e.g., attaching, tying, tethering, adhering, etc.) of analyte 22 at fluid-sensor interface 24 and charge transfer modulation therefrom. Sensing element 16 may comprise any suitable semiconducting (e.g., semi-insulating) material that allows for signal transduction and modulation between electrodes 18(1)-18(3) and analyte 22. In a general sense, the properties of the semiconducting material that provide for its semiconductive characteristics depend on a number of electrons in that material available to move freely through the material under the influence of an externally applied electric field. Any suitable semiconducting material appropriate to the assay protocol may be used within the broad scope of the embodiments. For example, a stack formed with ZnO thin films can be functionalized with selective linker chemistry (e.g., thiol, carboxylic, amine, etc.) to conjugate with (e.g., bind to) specific target species of analyte 22. The molecules facilitating the linker chemistry are referred to as capture probes; the capture probes can comprise proteins or small molecules (e.g., antibodies, nucleic acids, etc.) that can detect a specific target species of analyte 22; the capture probes may be immobilized on the surface of sensing element 16 at fluid-sensor interface 24.

An example material of semiconducting material used in sensing element 16 is zinc oxide (ZnO). Other examples include diamond (C), silicon (Si), germanium (Ge), tin (Sn), silicon carbide (SiC), Sulphur (Ss), boron nitride (BN), boron phosphide (BP), boron arsenide (BAs, $Ba_{12}As_2$), aluminum nitride (AlN), aluminum phosphide (AlP), aluminum arsenide (AlAs), aluminum antomonide (AlSb), gallium nitride (GaN), gallium phosphide (GaP), gallium arsenide (GaAs), gallium antimonide (GaSb), indium nitride (InN), indium phosphide (InP), indium arsenide (InAs), indium antimonide (InSb), cadmium selenide (CdSe), cadmium sulphide (CdS), cadmium telluride (CdTe), zinc selenide (ZnSe), zinc sulfide (ZnS), zinc telluride (ZnTe), cuprous chloride (CuCl), copper sulfide ($Cu_2S$), lead selenide (PbSe), lead sulfide (PbS), lead telluride (PbTe), tin sulfide (SnS), tin sulfide ($SnS_2$), tin telluride (SnTe), lead tin telluride (PbSnTe), thallium tin telluride ($Tl_2SnTe_5$), thallium germanium telluride ($Tl_2GeTe_5$), bismuth telluride ($Bi_2Te_3$), cadmium phosphide ($Cd_3P_2$), cadmium arsenide ($Cd_3As_2$), cadmium antimonide ($Cd_3Sb_2$), zinc phosphide ($Zn_3P_2$), zinc arsenide ($Zn_3As_2$), zinc antimonide($Zn_3Sb_2$), titanium dioxide ($TiO_2$), cuprous oxide ($Cu_2O$), cupric oxide (CuO), uranium dioxide ($UO_2$), uranium trioxide ($UO_3$), bismuth trioxide ($Bi_2O_3$), tin dioxide ($SnO_2$), barium titanate ($BaTiO_3$), strontium titanate ($SrTiO_3$), lithium niobate ($LiNbO_3$), lanthanum copper oxide ($La_2CuO_4$), lead iodide ($PbI_2$), molybdenum disulfide ($MoS_2$), gallium selenide (GaSe), tin sulfide (SnS), bismuth sulfide ($Bi_2S_3$), gallium manganese arsenide (GaMnAs), indium manganese arsenide (InMnAs), cadmium manganese telluride (CdMnTe), lead manganese telluride (PbMnTe), lanthanum calcium manganite ($La_{0.7}Ca_{0.3}MnO_3$), ferric oxide (FeO), nickel oxide (NiO), chromium bromide ($CrBr_3$), copper zinc tin sulfide (CZTS), tungsten sulfide ($WS_2$), tungsten selenide ($WSe_2$), vanadium dioxide ($VO_2$), graphene oxide, etc.

In various embodiments, electrodes 18(1)-18(3) may comprise any suitable conducting material, such as copper or gold, that does not react with fluid 20. In various embodiments, electrodes 18(1)-18(3) form Ohmic (e.g., resistive) electrical contact with sensing element 16. In various embodiments, fluid 20 may comprise any suitable fluid including liquids, gels, colloids, gases and/or combination thereof. Examples of fluid 20 include body fluids, such as sweat, blood, tears, serum, saliva, urine, etc.; and non-body fluids such as vapors (from fruits, milk, and other foods), aqueous and non-aqueous solutions, etc. Analyte 22 may correspond to various biomolecules being tested, such as glucose, lactose, ethylene, urea, salt (NaCl), etc.

Binding of analyte 22 at fluid-sensor interface 24 may occur through electro-chemical, electro-ionic, polarization, and other charge-based modes that causes work function tuning of the semiconducting material of sensing element 16, resulting in modulation of space-charge capacitance and electrical double layer capacitance. (Note that work function of a semiconductor material is a property of a surface of the material, and corresponds to a minimum energy required to remove an electron from an interior of the material to a point immediately above the surface of the material; the term "immediately" referencing a distance that is large in atomic scale, but small in terms of electrical fields). In a general sense, semiconductor interfaces, such as fluid-sensor interface 24 in fluid 20 comprising ions, experience disparate electrochemical potential at fluid-sensor interface 24.

At equilibrium, an exchange of charges occurs between sensing element 16 and fluid 20 resulting in charge redistribution at fluid-sensor interface 24. The localized charge redistribution in sensing element 16 is referred to as space-charge capacitance ($C_{sc}$); the localized charge redistribution in fluid 20 comprises the electrical double layer (EDL) capacitance ($C_{edl}$). The space-charge capacitance is typically a function of the semiconductor material of sensing element 16; different semiconductor materials exhibit different space-charge capacitances to the same electric field. Hence a measured total capacitance across fluid-sensor interface 24 at equilibrium derives from the material-specific space-charge capacitance and a capacitive impedance associated with molecules in the EDL binding to fluid-sensor interface 24.

Typically, EDL capacitance of fluid 20 may be negligible compared to the space-charge capacitance (i.e. $C_{edl} \gg C_{sc}$) of sensing element 16. However, where biochemical binding events occur at fluid-sensor interface 24 in confined spaces due to fluid containment by portion 14B of substrate 14, the EDL capacitance can be significant and matched in magnitude to the space-charge capacitance (i.e. $C_{edl} \approx C_{sc}$). In some embodiments, for example, where the EDL capacitance is matched in magnitude to the space-charge capacitance, changes to the EDL capacitance with varying concentrations of analyte 22 may be proportionally reflected in similar changes to the space-charge capacitance. Confinement of fluid 20 to an active area of biosensor 12 may enhance the charge transfer between sensing element 16 and fluid 20 and consequent effects. The confinement may be achieved through suitably sized pores 26 in substrate 14 (e.g., using a porous membrane, such as in portion 14B).

Further, the total capacitance across fluid-sensor interface 24 may vary with the binding interactions at fluid-sensor interface 24; the binding interactions may vary with the specific molecule binding to sensing element 16. Tunable electron-ionic mechanisms resulting from the biochemical binding events within the confined spaces at fluid-sensor interface 24 may be measured and/or characterized using electrical parameters, such as current, voltage, impedance and capacitance. In some embodiments, input voltages are applied; in other embodiments, current sources are used to generate desired voltages across electrodes 18(1)-18(3); in yet other embodiments, a steady state potential of different amounts is maintained across electrodes 18(1)-18(3). Output 19 from biosensor 12 may include impedance in some embodiments; current in other embodiments; and capacitance in yet other embodiments. Some embodiments of biosensing system 10 can tune biosensor 12 to distinguish between capacitance changes from biochemical analyte binding and from space charge modulation.

In various embodiments, fluid-sensor interface 24 comprises a portion of the EDL. In some embodiments, the sensitivity of biosensor 12 may vary with the EDL thickness; a particular EDL thickness may be conducive to detect a corresponding target species of analyte 22. The height of fluid-sensor interface 24 may be indicative of a volume of fluid 20 above the surface of sensing element 24 and can correlate with the sensitivity of biosensor 12; for example, height $h_1$ of fluid-sensor interface 24 may correspond to high sensitivity detection of glucose, but low sensitivity detection of cortisol; height $h_2$ of fluid-sensor interface 24 may correspond to high sensitive detection of cortisol, but low sensitivity detection of glucose; etc.

In some embodiments, electrokinetic focusing using polarization principles may be used to achieve particle separation (e.g., screening) in fluid 20, which may further enhance EDL capacitance modulation and/or sensitivity of biosensor 12. In a general sense, the EDL varies based on the presence or absence of specific target biomolecules in fluid 20. Charge modulation in the EDL may be further controlled by applying an orthogonal electric field (with respect to transverse electrodes 18(1) and 18(2)) to sensing element, forming an electrically modulated gate. In some embodiments, the transverse electric field provides a bias voltage (e.g., around which the response of biosensor 12 may be linear, gain may be high, etc.) and the orthogonal electric field provides a measure of the capacitance of the EDL. The orthogonal electric field can also enable pinning of the EDL and tuning a height of an electro-ionic interface height (e.g., height of fluid-sensor interface 24 including the EDL), facilitating segmenting the EDL capacitance and the space-charge capacitance enabling higher sensitivity of biosensor 12.

Because the capacitance is influenced by frequency of the electric field, AC voltage of varying amplitude and frequency may be applied to orthogonal electrodes 18(1) and 18(3) to cause changes to capacitance that can be measured with higher sensitivity. Embodiments of biosensing system 10 can facilitate separately detecting and characterizing multiple different target species of analyte 22 using the same biosensor 12, for example, by varying the orthogonal electric field with respect to the transverse electric field. The orthogonal electric field, generated between orthogonal electrodes 18(1) and 18(3) may facilitate differentiation of target species of analyte 22 from each other; for example, orthogonal electric field $E_1$ generated using AC voltage of amplitude $V_1$ and frequency $f_1$ may cause target species $S_1$ to migrate to fluid-sensor interface 24; another orthogonal electric field $E_2$ generating using AC voltage of amplitude $V_2$ and frequency $f_2$ may cause target species $S_2$ to migrate to fluid-sensor interface 24; and so on.

In some embodiments, transverse electrodes 18(1) and 18(2) are fabricated on porous membranes comprising portion 14B of substrate 14 and passivated for electrical isolation with a dielectric comprising portion 14A of substrate 14. Semiconductor material, such as ZnO, graphene, $MoS_2$, $VO_2$, etc. of sensing element 16 is deposited across transverse electrodes 18(1) and 18(2) to provide a desired surface area for biochemical binding events. Orthogonal electrode 18(3) is deposited on a surface of sensing element 16, distal from the surface where the binding reactions occur, for example, to electrically modulate the surface charge distribution and gate the flow of charges across transverse electrodes 18(1) and 18(2).

Embodiments of biosensing system 10 can include nanoporous and/or nanostructure materials for performing real-time detection of analyte 22 in fluid 20. The nanoporous and/or nanostructure material may allow wicking of fluid 20 and also enhance detection of specific biochemical binding events on the semiconducting material surface of sensing element 16 without charge screening from non-specific constituents in fluid 20. In some embodiments, a Debye length (e.g., a measure of a charge carrier's net electrostatic effect in solution, comprising a length along which the electrostatic effects persist; the Debye length is generally a radius of a sphere outside of which charges are screened) formed at fluid-sensor interface 24 may be maximized; the Debye length may be measured and quantified as the EDL (e.g., the Debye length is indicative of a thickness of the EDL). Debye length measurement and tuning may be performed with orthogonal electrodes 18(1) and 18(3). In various embodiments, baseline 19(1) may be indicative of a baseline value for the Debye length. The transverse and orthogonal electric fields, which are mutually perpendicular to each other, may facilitate detecting and characterizing multiple target species irrespective of their charge status. Further, the orthogonal electric field may be tuned to manipulate and/or measure various Debye lengths of the EDL in fluid 20, facilitating isolation of different target species according to the Debye length.

In some embodiments, EDL probing may facilitate understanding of molecular information in fluid 20, and may be suitable for ultra-low power electronics. In various embodiments, the charge screening effects may be characterized by various models (e.g., theories), including Helmholtz model, Gouy-Chapman model, and Gouy-Chapman-Stern model. For example, according to the Gouy-Chapman-Stern model, the EDL may be characterized as a capacitance in an electrical circuit, the capacitance varying according to predetermined functions (e.g., relationships, formulae) of material properties and molecular constituents of fluid 20.

In various embodiments, biosensor 12 can operate in ultra-low power modes, and can detect and/or diagnose concentration of analyte 22 for various modes of operation, including: single-species (e.g., analyte 22 comprises a single target species of interest), single input/output (I/O) mode, single-use (e.g., biosensor 12 discarded after single use); single-species, multi-I/O mode, single-use; multi-species (e.g., analyte 22 comprises more than one target species of interest), single-I/O mode, single-use; multi-species, multi-I/O mode, single-use; single-species, single-I/O mode, multi-use (e.g., biosensor 12 reusable for multiple tests); single-species, multi-I/O mode, multi-use; multi-species, single-I/O mode, multi-use; multi-species, multi-I/O mode, multi-use.

In some embodiments, analog-to-digital signal conversion may be employed for sensing and processing output 19 (e.g., baseline 19(1) and response 19(2)) from sensing element 16. In other embodiments, digital to analog signal conversion may be employed for sensing and processing. In yet other embodiments, mixed signal circuits may be employed for sensing and processing. Data communication with an end user may be included in biosensing system 10, for example, to convert analog or digital signals to meaningful user information (e.g., impedance changes in sensing element 16 converted into digital signals, which in turn are converted into a readout of target species concentration level on a display).

In some embodiments, output 19 may be communicated (e.g., through wired or wireless mechanisms) to smart portable devices, and other computing devices, for example, for further analysis. In other embodiments, output 19 may be communicated (e.g., through wired or wireless mechanisms) to light based display devices (e.g., light emitting diode (LED) display, OLED etc. based status displays)

Embodiments of biosensing system 10 may be used to detect and/or analyze presence and/or concentration of various suitable molecules that react in the presence of electrochemical/ionic binding at fluid-sensor interface 24. Example uses include small and thin form-factor biosensor applications (e.g., non-invasive/minimally invasive diagnostics procedures), such as pin-prick strips, catheters probe tips, and body patches for detection of disease markers (glucose, cardiac, cancer, neural, infection, etc.), etc.; food packaging and monitoring; etc.

Embodiments of biosensing system 10 may be included with "detect-to-warn" and "detect-to-treat" features that can perform ultra-sensitive and highly specific detection of target agents in a non-invasive manner. In some embodiments, the analysis and quantification may be performed in real-time and data transmitted using near-field communications from user to desired locations (e.g., wearable units, hand held units, personal computing devices, medical monitoring units, etc.)

Biosensor 12 may be provisioned on various types of substrate 14 (e.g., rigid and flexible such as silicon, glass, printed circuit boards, polyurethane, polycarbonate, polyamide, and polyimide, etc.) for example, to facilitate continuous and real-time detection, monitoring, and quantification of chemical and biological agents in body fluids (e.g., blood, sweat, tears, urine, saliva, etc.) Real-time detection can be performed in single-use manner or continuous-use manner using the bio sensor technology of biosensing system 10.

Note that the numerical and letter designations assigned to the elements of FIG. 1 do not connote any type of hierarchy; the designations are arbitrary and have been used for purposes of teaching only. Such designations should not be construed in any way to limit their capabilities, functionalities, or applications in the potential environments that may benefit from the features of biosensing system 10. It should be understood that biosensing system 10 shown in FIG. 1 is simplified for ease of illustration.

Figure 2:
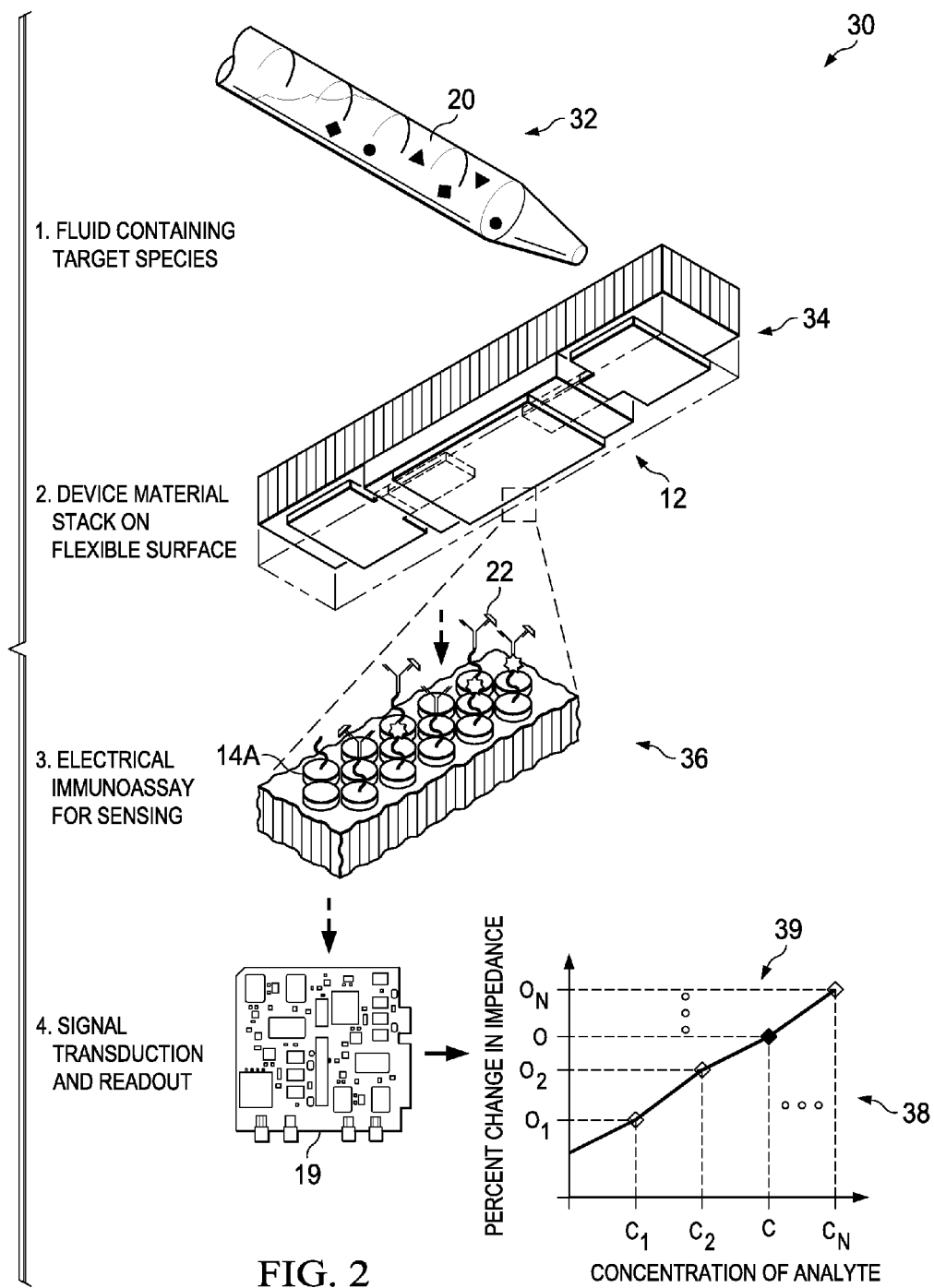
FIG. 2 is a simplified block diagram illustrating other example details of embodiments of the biosensing system.

Turning to FIG. 2, FIG. 2 is a simplified block diagram illustrating example operations 30 according to an embodiment of biosensing system 10. During operation, biosensor 12 may be immersed in, or otherwise brought into contact with fluid 20 at 32. At 34, transverse voltage may be applied across transverse electrodes 18(1) and 18(2) and orthogonal voltage may be applied across orthogonal electrodes 18(1) and 18(3). The transverse voltage and orthogonal voltage generate electric fields in mutually perpendicular directions.

In a general sense, upon application of an electric field between orthogonal electrodes 18(1) and 18(3), an EDL may be generated in fluid 20. In some embodiments, the orthogonal voltage may comprise AC voltage. Such AC voltage may cause analyte 22 to additionally move normal (e.g., perpendicular, orthogonal) to the applied AC electric field direction, in a plane parallel to transverse electrodes 18(1) and 18(2), affecting the current flowing therebetween. In a general sense, the effect of AC electric fields on analyte 22 can be controlled by adjusting electric field parameters, such as amplitude, frequency, wave symmetry and phase of the AC voltage.

Further, the electric field generated by the transverse electric voltage applied across electrodes 18(1) and 18(2) may enable dielectrophoresis (DEP), in which analyte 22 is attracted to or repelled from a region of high electric field intensity in a direction perpendicular to the plane of transverse electrodes 18(1) and 18(2), thereby focusing analyte 22 at fluid-sensor interface 24. In some embodiments, an AC voltage may be initially applied across transverse electrodes 18(1) and 18(2), enabling DEP and focusing analyte 22 to fluid-sensor interface 24 at sensing element 16; subsequent switching of the voltage across transverse electrodes 18(1) and 18(2) from AC to DC, with the AC voltage across orthogonal electrodes 18(1) and 18(3) facilitates formation of the EDL in fluid 20 and modulation of current across transverse electrodes 18(1) and 18(2). Note that in some embodiments, the orthogonal voltage may also comprise DC voltage; in such embodiments, the modulation of the current between transverse electrodes 18(1) and 18(2) may not be as large as with AC voltage; nevertheless, such modulation may be sufficient to enable detection of at least a single target species of analyte 22.

At 38, a binding of analyte 22 to fluid-sensor interface 24 may be sensed (e.g., measured) through a change in impedance, capacitance, current, or voltage across sensing element 16 based on electron-ion interactions at fluid-sensor interface 24. In various embodiments, output 19 (e.g., change in impedance, current, voltage, etc.) from biosensor 12 may vary with presence, concentration and/or other characteristic of analyte 22. Output 19 may be measured using any known technique, such as potentiostat, amperometer, etc. depending on a type of output 19 (e.g., whether change in impendence, or current, etc.)

In various embodiments, biosensor 12 may be initially calibrated at 38 for a specific analyte through suitable calibration steps (e.g., fluid calibration and electronic calibration). For example, fluid 20 may comprise a liquid containing analyte 22 in a known concentration, say $C_1$. The transverse and orthogonal voltages may be applied across electrodes 18(1)-18(3) and output 19 measured to be, say $O_1$. Output 19 may comprise impedance in some embodiments, as illustrated in the figure. Output 19 may also comprise any other suitable measurement, including capacitance, current, etc. In some embodiments, $O_1$ may comprise response 19(2). In other embodiments, $O_1$ may comprise a suitable combination of baseline 19(1) and response 19(2). Next, concentration of analyte 22 may be changed in fluid 20 to another known concentration, say $C_2$. The transverse and orthogonal voltages may be applied across electrodes 18(1)-18(3) and output 19 measured to be, say $O_2$. The process may be continued until a range of concentrations has been measured, from $C_1$ to $C_N$. A calibration chart 39 may be generated with analyte concentrations $C_1, C_2, \ldots C_N$ charted against corresponding outputs $O_1, O_2, \ldots O_N$. Calibration chart 39 may provide an expected analyte concentration (within range $C_1$-$C_N$), for a known output (within range $O_1$-$O_N$), and vice versa. After testing with an unknown analyte concentration to obtain corresponding output 19, say O, the calibration chart may be used to obtain the corresponding analyte concentration, C, therefrom. Although one particular calibration technique has been described herein, any suitable calibration technique may be used within the broad scope of the embodiments.

Figure 3:
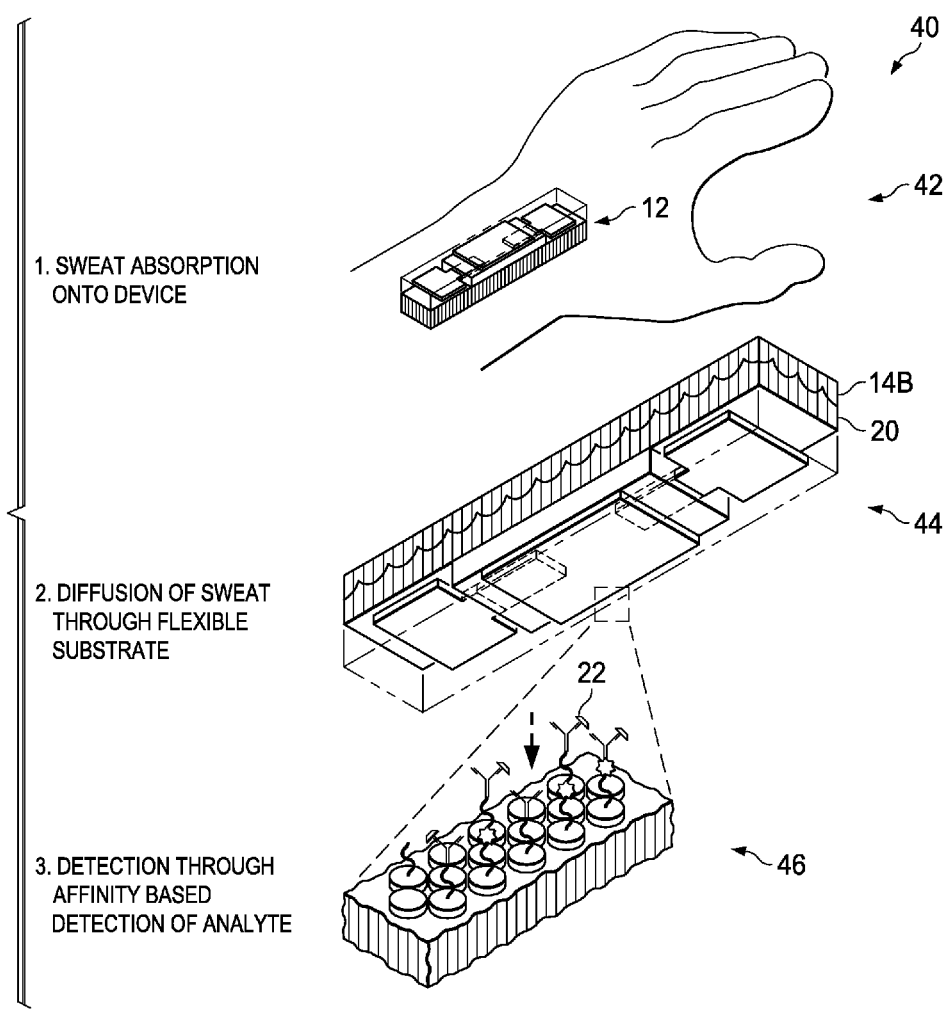
FIG. 3 is a simplified block diagram illustrating yet other example details of embodiments of the biosensing system.

Turning to FIG. 3, FIG. 3 is a simplified block diagram illustrating example operations 40 that may be associated with an embodiment of biosensing system 10. At 42, biosensor 12 may be attached (e.g., removably, for example, using an appropriate adhesive) to skin. Sweat, comprising fluid 20, may diffuse through the porous membrane portion 14B of substrate 14 at 22. At 46, transverse and orthogonal voltages may be applied to electrodes 18(1)-18(3), resulting in electron-ion interaction between analyte 22 (e.g., salt) in fluid 20 and sensing element 16 at fluid-sensor interface 20. The interaction may be sensed through a change in output 19, which may indicate an amount of analyte 22 in the sweat.

Note that a similar procedure may be followed to measure any suitable secretion, including tears. In a general sense, sweat may be noisier than tears. Similar procedures may be followed for blood testing using a finger prick, similar to a glucose sensor; urine testing using a test strip comprising biosensor 12, similar to a typical pregnancy tester; and saliva testing with biosensor 12 inserted into a mouth guard or similar device.

Figure 4:
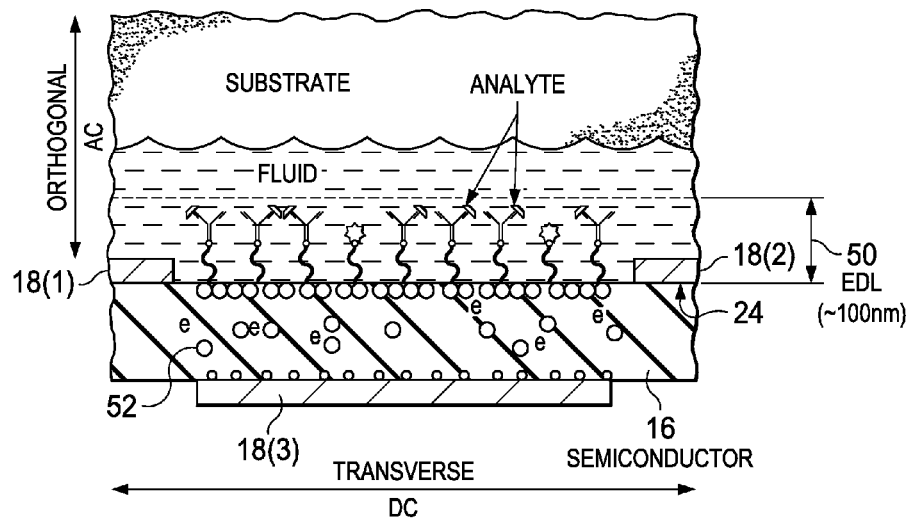
FIG. 4 is a simplified block diagram illustrating yet other example details of embodiments of the biosensing system.

Turning to FIG. 4, FIG. 4 is a simplified block diagram illustrating example details according to an embodiment of biosensing system 10. A porous membrane of portion 14B of substrate 14 may allow fluid 20 to contact sensing element 16 along fluid-sensor interface 24 through pores 26. A transverse voltage is applied across sensing element 16 between transverse electrodes 18(1) and 18(2). An orthogonal voltage is applied across sensing element in a direction perpendicular to the transverse voltage across electrodes 18(1) and 18(3). In some embodiments, the transverse voltage is direct current (DC) voltage, whereas the orthogonal voltage is alternating current (AC) voltage.

The biological target molecule, comprised in analyte 22, reaches fluid-sensor interface 24 through portion 14B of substrate 14 and generates an electrical output based on its presence, concentration, or other characteristic. In various embodiments, the voltage across sensing element 16 modulates the electrical field at fluid-sensor interface 24, causing polarization of charges and generation of capacitance of EDL 50 in fluid 20 and capacitance of space-charge 52 (also referred to as charge depletion layer) in sensing element 16 from binding of analyte 22 to fluid-sensor interface 24. Positive or negative charges are accumulated at fluid-sensor interface 24, depending on the type of semiconductor material of sensing element 16 (e.g., n-type, p-type, steady state potential (e.g., work function differences)) and the target species (e.g., negative, positive, or neutral) comprised in analyte 22 binding to fluid-sensor interface 24. Charge modulation occurs as a result of the applied electric fields and also from modification to the bound target species; the charge modulation is measured as output 19, for example, through a change in current flow, or as impedance of the circuit.

Figure 5:
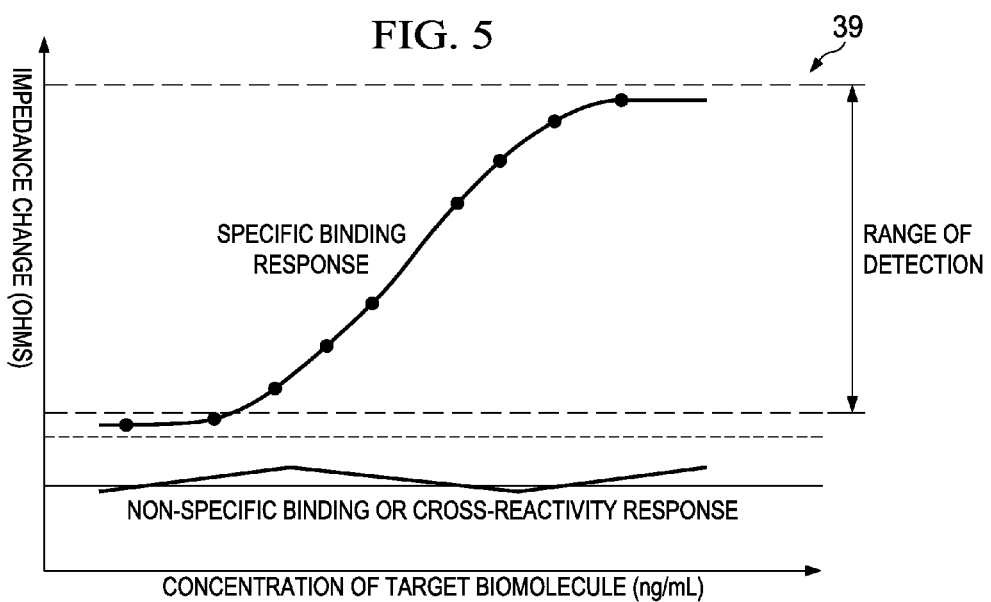
FIG. 5 is a simplified block diagram illustrating yet other example details of embodiments of the biosensing system.

Turning to FIG. 5, FIG. 5 is a simplified diagram illustrating an example calibration chart 39 according to an embodiment of biosensing system 10. According to calibration chart 39, the concentration of a target species (e.g., target biomolecule) may be plotted along the X-axis in ng/mL; the corresponding impedance of sensing element 16 may be plotted along the Y-axis in ohms. Note that the Y-axis can plot any suitable output, including percentage change in impedance; capacitance; etc. Detection of a specific target species of analyte 22 is achieved through an affinity based mechanism, wherein the target species binds to sensing element 16 through specific capture molecules (e.g., synthetic DNA, Peptide nucleic acid (PNA), antibodies, etc.) The affinity binding produces charge perturbation at fluid-sensor interface 24 and can be measured as output 19. Sometimes, one or more interfering species other than the target species of analyte 22 can be present in fluid 20, which can also interact with fluid-sensor interface 24. Binding of the specific target species to fluid-sensor interface 24 is referred to as specific binding response; binding of the interfering species to fluid-sensor interface 24 is referred to as cross-reactivity response (or non-specific binding response). In some embodiments, the cross-reactivity response may be subtracted out of the specific binding response through appropriate logic circuits or algorithms.

In some embodiments, the change in measured impedance may be small for small concentrations; likewise, the change in measured impedance may be small when the concentration of the target species in fluid 20 is high. In other words, biosensor 12 may be tuned to provide greater sensitivity to concentrations of target species within a specific range. Such a zone of greater sensitivity may be referred to as a range of detection. In the range of detection, small changes in concentration may correspond to relatively large changes in measured impedance. The sensitivity of biosensor 12 to the target species may be tuned using various electrode designs, material selection for sensing element 16, and other parameters based on particular needs and availability.

Turning to FIGS. 6A-6C, FIGS. 6A-6C are simplified block diagrams illustrating example details of biosensor 12. Electrodes 18(1)-18(3) may comprise various nanostructures in a planar dimension. Spatial patterning of electrodes 18(1)-18(3) can affect the placement and shape of the planar aggregation of analyte 22 at fluid-sensor interface 24, thereby affecting the sensitivity of biosensor 12. For example, the specific shape of electrodes 18(1) and 18(2) can affect the impedance and thereby the ionic current in fluid 20 at the vicinity of fluid-sensor interface 24.

In FIG. 6A, electrodes 18(1) and 18(2), across which the transverse voltage is applied may be situated on the same plane. Each of electrodes 18(1) and 18(2) may comprise digits 54 that may extend over sensing element 16. Digits 54 may be parallel along the length and face each other over sensing element 16. Digits 54 may be tailored for particular electrical modulation properties desired for specific target species of analyte 22. For example, in FIG. 6B, each of electrodes 18(1) and 18(2) may comprise digits 54 that are offset from each other along their widths and overlap along their lengths. In FIG. 6C, each of electrodes 18(1) and 18(2) may comprise a plurality of interleaving digits 54, overlapping along their lengths and offset along their widths. Note than any number of digits 54 (or other design features of electrodes 18(1)-18(3)) may be included within the broad scope of the embodiments.

Figure 7:
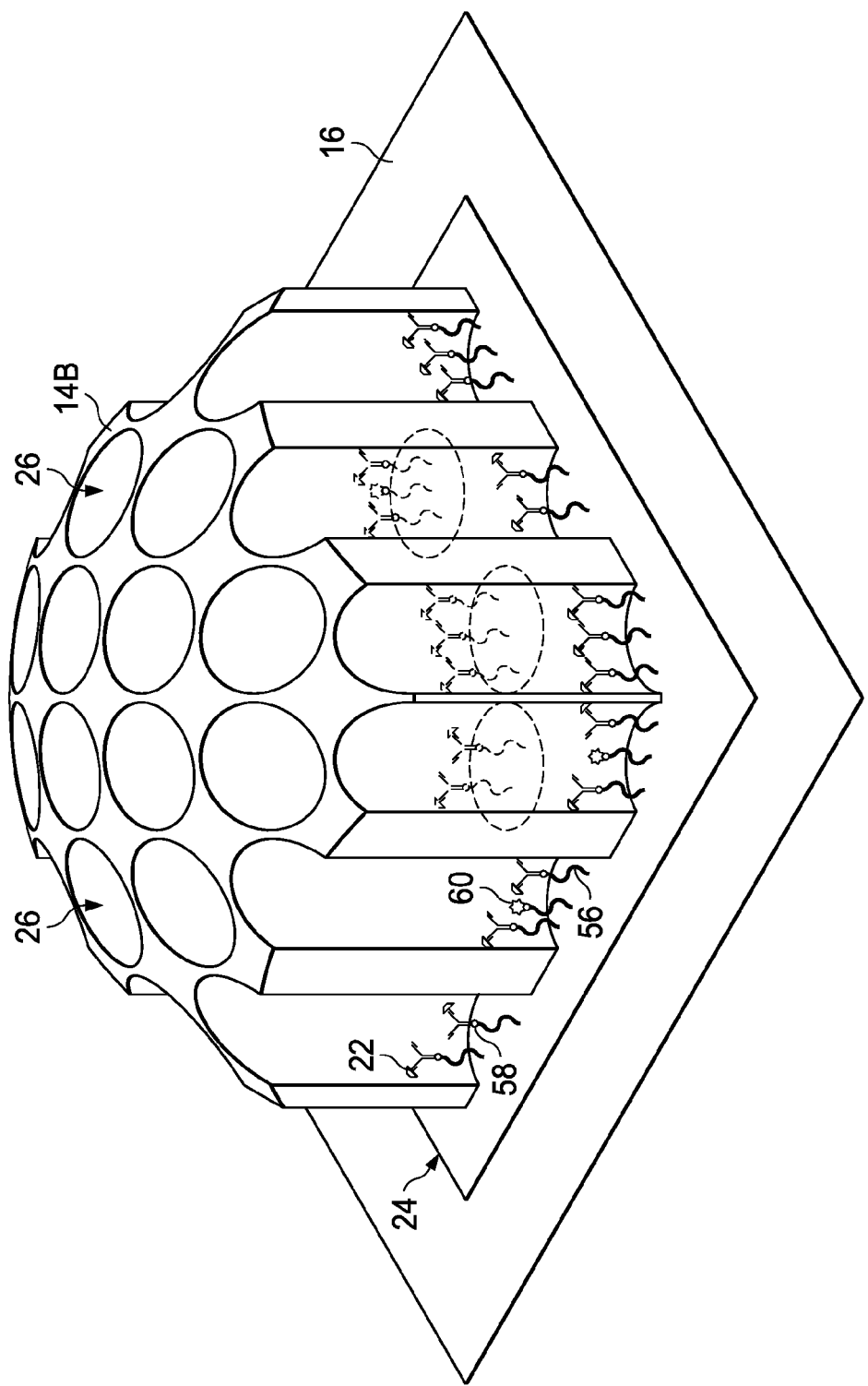
FIG. 7 is a simplified block diagram illustrating yet other example details of embodiments of the biosensing system.

Turning to FIG. 7, FIG. 7 is a simplified block diagram illustrating example details associated with binding according to an embodiment of biosensing system 10. Based on the method and physical conditions used for deposition of sensing element 16, selective surface tuning can be achieved thereon, for example, to enhance sensitivity of biosensor 12 to specific target species of analyte 22. In an example embodiment, in which sensing element 16 comprises ZnO, enriched zinc terminated sites or enriched oxygen terminated sites may be deposited on ZnO, for example. The Zn-terminated site and the O-terminated sites can influence immobilizing of biomolecular capture probes based on preferential binding of linker molecules to either Zn-terminated sites or O-terminated sites. Such mechanisms can improve efficiency and sensitivity of biosensor 12. Note that other embodiments can include Graphene oxide or $MoS_2$ instead of ZnO.

In some embodiments, analyte 22 may bind directly to sensing element 16 at fluid-sensor interface 24. In other embodiments, to achieve affinity binding of target species, the surface of sensing element 16 comprising fluid-sensor interface 24 is functionalized with various linker molecules 56. Analyte 22 binds to linker molecules 56, effecting charge modulation at fluid-sensor interface 24. Dithiobis succinidyl propionate is an example of a thiol linker molecule 56. Any other suitable linker molecule, such as carboxylic molecules, hydroxyl molecules, etc. may be used within the broad scope of the embodiments.

In yet other embodiments, to achieve affinity binding of target species, the surface of sensing element 16 comprising fluid-sensor interface 24 is functionalized with various linker molecules 56, to which capture probes 58 are bound. Although additional molecules may be bound to capture probes 58, and so on, beyond three levels of binding, the charge modulation and characterization signal may become weak and difficult to isolate from noise, affecting sensitivity of biosensor 12. Capture probes 58 may connect linker molecules 56, which are attached to the surface of sensing element 16, to analyte 22. Examples of capture probes 58 includes aptamers, antibodies, enzymes, peptides, and amino acid and nucleic acid sequences.

In some embodiments, blocking molecules 60 may neutralize linker molecules 56 without capture probes 58 and minimize binding of interfering species that can cause signal attenuation and cross-reactivity responses. Examples of blocking molecules 60 include SuperBlock™, albumin based solutions that can block unbound organic —NH groups on linker molecules 56.

Note that for ease of illustration, pore 26 is illustrated as a through-hole pore. Various other pore configurations may be included within the broad scope of the embodiments. For example, pore 26 may comprise intercalated pores in some embodiments. In other embodiments, pore 26 may comprise hierarchical pores (e.g., pore in pore). Various commercially available materials may be used to fabricate substrate 14 to include suitable pore configurations. For example, Merocel™ is one of a commercially available porous material of the intercalated "sponge" like material. Other commercially available materials include those sold by Whatman Membranes™ from GE Life Sciences™, Advantec™, etc. Hierarchical pores may be seen in diatoms, and similar pore configuration used in synthesizing appropriate substrate materials.

Figure 8:
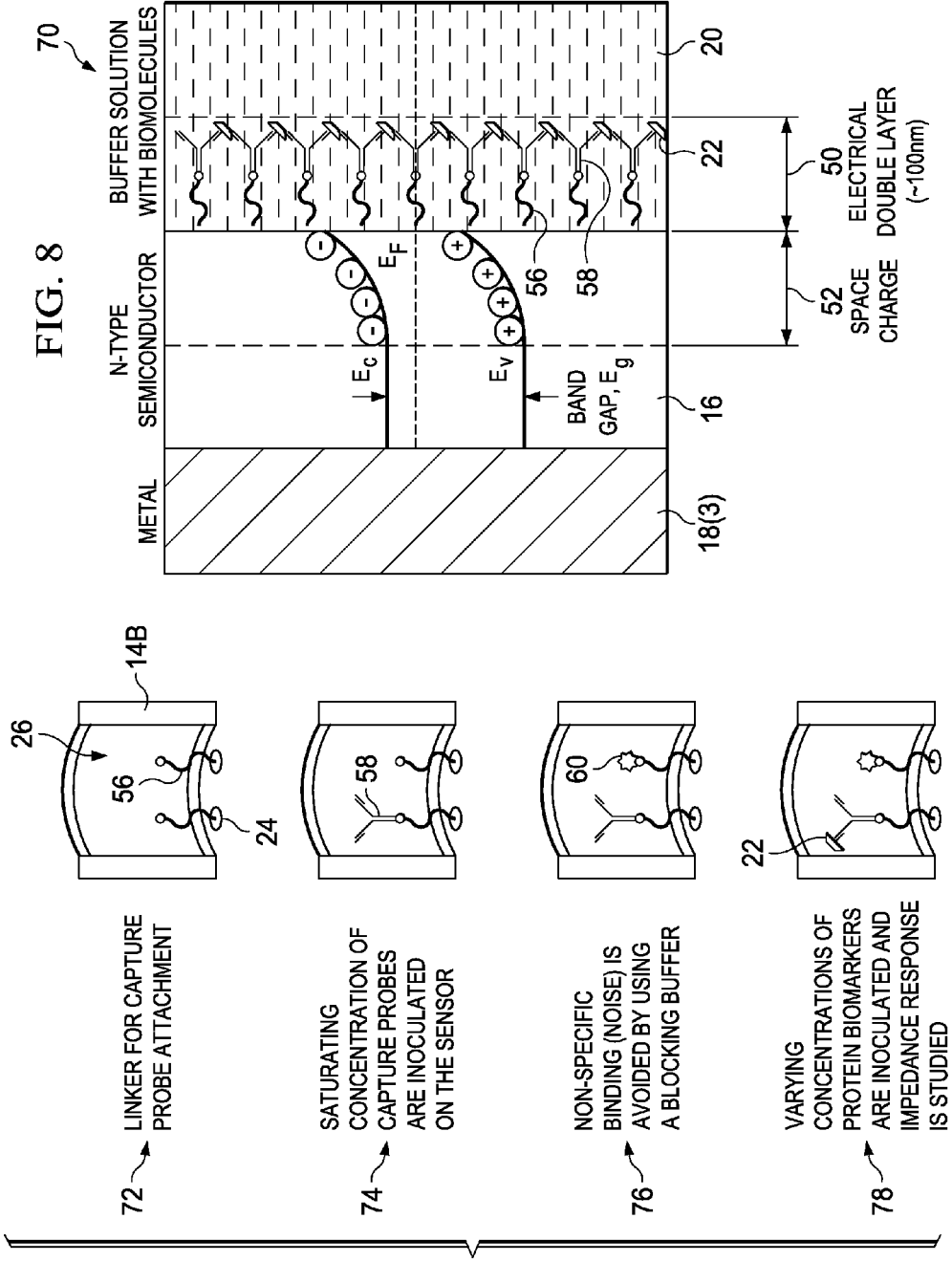
FIG. 8 is a simplified block diagram illustrating yet other example details of embodiments of the biosensing system.

Turning to FIG. 8, FIG. 8 is a simplified diagram illustrating example operations 70 and details according to an embodiment of biosensing system 10. At 72, linker molecule 56 (e.g., dithiobis succinimidyl propionate) may be bound to the surface of sensing element 16 at fluid-sensor interface 24, comprising the surface of sensing element 16 that can be exposed to fluid 20. At 74, a saturating concentration (e.g., maximum concentration loadable onto sensing element 16) of capture probes 58 may be inoculated (e.g., introduced, such as with a fixed volume of solution, in a metered manner) on biosensor 12. Capture probes 58 bind to at least some linker molecules 56. At 76, non-specific binding noise may be avoided by adding a blocking buffer containing blocking molecules 60. At 78, varying concentrations of analyte 22 (e.g., protein biomarkers) are inoculated and impedance response is studied to generate calibration chart 39.

An example cross-section is also shown, comprising gold electrode 18(3) in Ohmic contact with n-type metal oxide semiconductor sensing element 16, which is in contact with fluid 20. The electrical voltage supplied to sensing element 16 may provide sufficient energy to polarize fluid 20 and activate sensing element 16. Charge depletion layer 52 and electrical double layer 50 may vary in size and electrical properties based on the binding interaction between analyte 22 and sensing element 16 at fluid-sensor interface 24. Note that charge depletion layer 52 indicates modulation of electro-ionic charge distribution at fluid-sensor interface 24. In the example embodiment shown, sensing element 16 is a n-type semiconductor and at steady state, the energy bands of the semiconductor material of sensing element 16 are bent to align Fermi levels, resulting in charge build-up on the semiconductor side of fluid-sensor interface 24. Charge depletion layer 52 may also be referred to in this Specification as the "space charge" region. Conversely, for a p-type semiconductor material of sensing element 16, the space charge region is formed by energy band bending in the opposite direction. In a general sense, the space charge region forms in response to distortion of the semiconductor material's valence and conduction bands ("band bending") in the vicinity of fluid-sensor interface 24.

Figure 9:
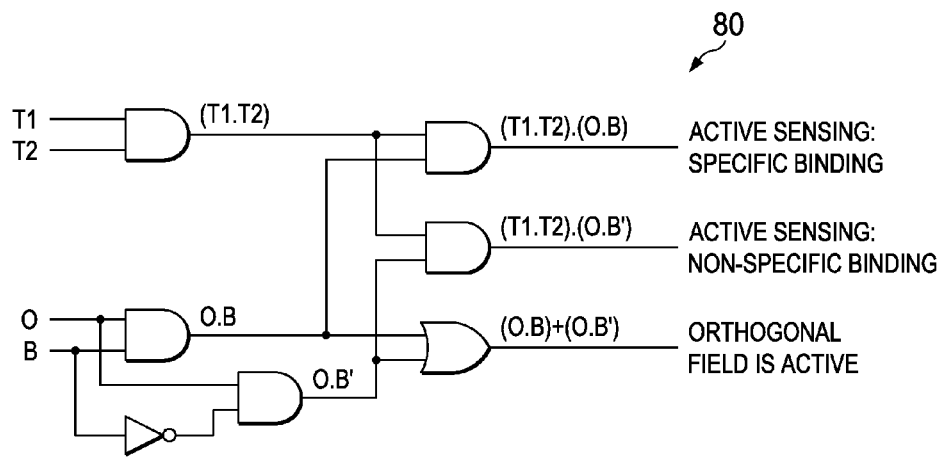
FIG. 9 is a simplified circuit diagram illustrating yet other example details of embodiments of the biosensing system.

Turning to FIG. 9, FIG. 9 is a simplified circuit diagram illustrating example details of a digital logic circuit 80 representing an embodiment of biosensing system 10. Digital logic circuit 80 facilitates communicating output 19 in a user readable format. In some embodiments, digital logic circuit uses digitized analog signal as inputs. T1 and T2 represent an electrode pair (e.g., electrodes 18(1) and 18(2)) applying an analog voltage signal to biosensor 12. O represents the orthogonal voltage input by electrode 18(3), and corresponds to a clock/power signal indicating the operational state of biosensor 12. B represents the signal corresponding to modulation to the electric field at fluid-sensor interface 24 from a specific target species; the B signal may be digitized to 0 to indicate absence of the target species and 1 to indicate presence of the target species. B' represents the signal due to any non-specific molecule or binding in the absence of the target species. The output from digital logic circuit 80 may be input to a microcontroller (not shown).

Digital logic circuit 80 makes a decision regarding the presence or absence of the target species based on user-defined (e.g., predetermined) inputs T1,T2 and O and measured signal B. Output (T1.T2).(O.B) represents active sensing of binding of target species with a 0 signal indicating absence of the target species, and a 1 signal indicating presence of the target species; output (T1.T2).(O.B') represents active sensing of binding of any non-target species with a 0 signal indicating absence of the non-target species, and a 1 signal indicating presence of the non-target species; and output (O.B).(O.B') represents whether the orthogonal voltage field is active, with a 0 signal indicating that the field is not active, and a 1 signal indicating that the field is active.

Figure 10:
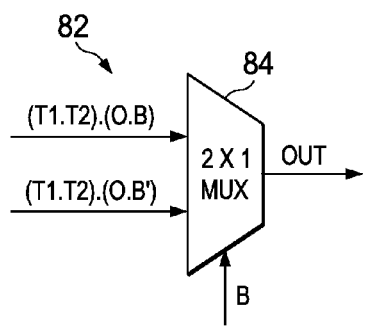
FIG. 10 is a simplified circuit diagram illustrating yet other example details of embodiments of the biosensing system.

Turning to FIG. 10, FIG. 10 is a simplified circuit diagram illustrating example details of a digital logic circuit 82 representing an embodiment of biosensing system 10. In some embodiments, a multiplexer 84 (e.g., an integrated circuit) may be used for decision making based on outputs of digital logic circuit 80. Output (T1.T2).(O.B) of digital logic circuit 80 may be input as 1 signal to multiplexer 84 when specific binding from target species occurs is detected and as 0 signal when non-specific binding occurs. Likewise, output (T1.T2).(O.B') of digital logic circuit 80 may be input as 1 when target species is not present and as 0 when target species is detected. An OUT signal is output from multiplexer; the OUT signal can digital 0 or 1 based on the presence or absence of the target species.

Turning to FIG. 11, FIG. 11 is a simplified diagram illustrating an example truth table 86 for multiplexer 84 of digital logic circuit 82 according to an embodiment of biosensing system 10. Column 86 represents a clock/power signal indicating the operational state of biosensor 12. Column 90 represents active sensing of binding of target species with a 0 indicating absence of the target species, and a 1 indicating presence of the target species. Column 92 represents active sensing of binding of any non-target species with a 0 indicating absence of the non-target species, and a 1 indicating presence of the non-target species. Column 94 represents the signal corresponding to modulation to the electric field at fluid-sensor interface 24 from a specific target species; the B signal may be digitized to 0 to indicate absence of the target species and 1 to indicate presence of the target species.

Column 96 represents the OUT signal of multiplexer 84 to the corresponding inputs as indicated in columns 88-94. Column 98 represents an interpretation by a microprocessor based on inputs and processed signal out from biosensor 12. The OUT signal from multiplexer 84 can be used to turn on a light emitting diode (LED) or other suitable display or indicator. The status of the indicator corresponding to the various inputs and outputs as indicated in respective rows is represented in column 100. Thus, according to truth table 86, if the orthogonal voltage has been turned on (O=1), and the target species is detected (B=1; (T1.T2)(O.B)=1), along with absence of non-target species ((T1.T2)(O.B')=0), the LED light turns on (LED output=ON).

Figure 12:
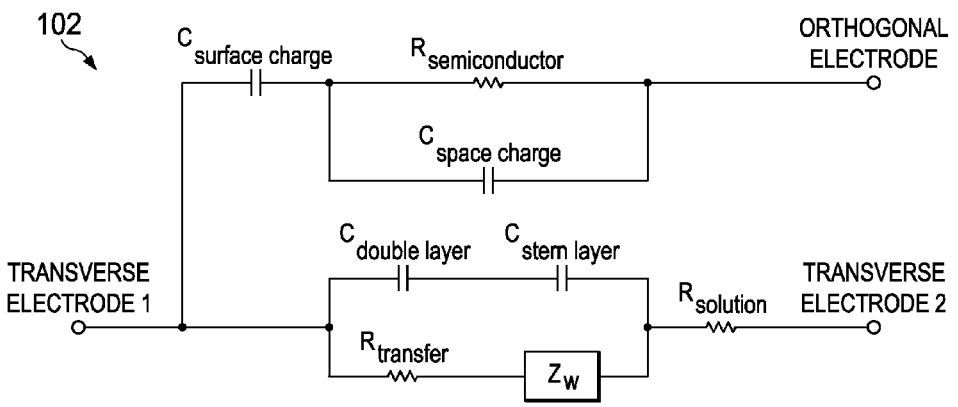
FIG. 12 is a simplified circuit diagram illustrating yet other example details of embodiments of the biosensing system.

Turning to FIG. 12, FIG. 12 is a simplified diagram illustrating an example circuit model 102 according to an embodiment of biosensing system 10. Equivalent circuit model 102 can be used to represent the three electrode configuration of biosensor 12 and comprehend output 19 comprising an analog signal measured at electrodes 18(1)-18(3). $C_{surface\ charge}$ represents capacitance of the surface charges at fluid-sensor interface 24; $R_{semiconductor}$ represents resistance of sensing element 16; and $C_{space\ charge}$ represents capacitance of charge depletion layer 52. $C_{surface\ charge}$, $R_{semiconductor}$ and $C_{space\ charge}$ influence signal output from biosensor 12 at orthogonal electrode 18(3). $C_{double\ layer}$ represents the capacitance of EDL 50; $C_{stern\ layer}$ represents capacitance of the Stern layer in fluid 20; $R_{transfer}$ and $Z_w$ represent resistive parameters of fluid 20 at fluid-sensor interface 24 that influence signal output from biosensor 12 as measured at transverse electrodes 18(1) and 18(2).

Figure 13:
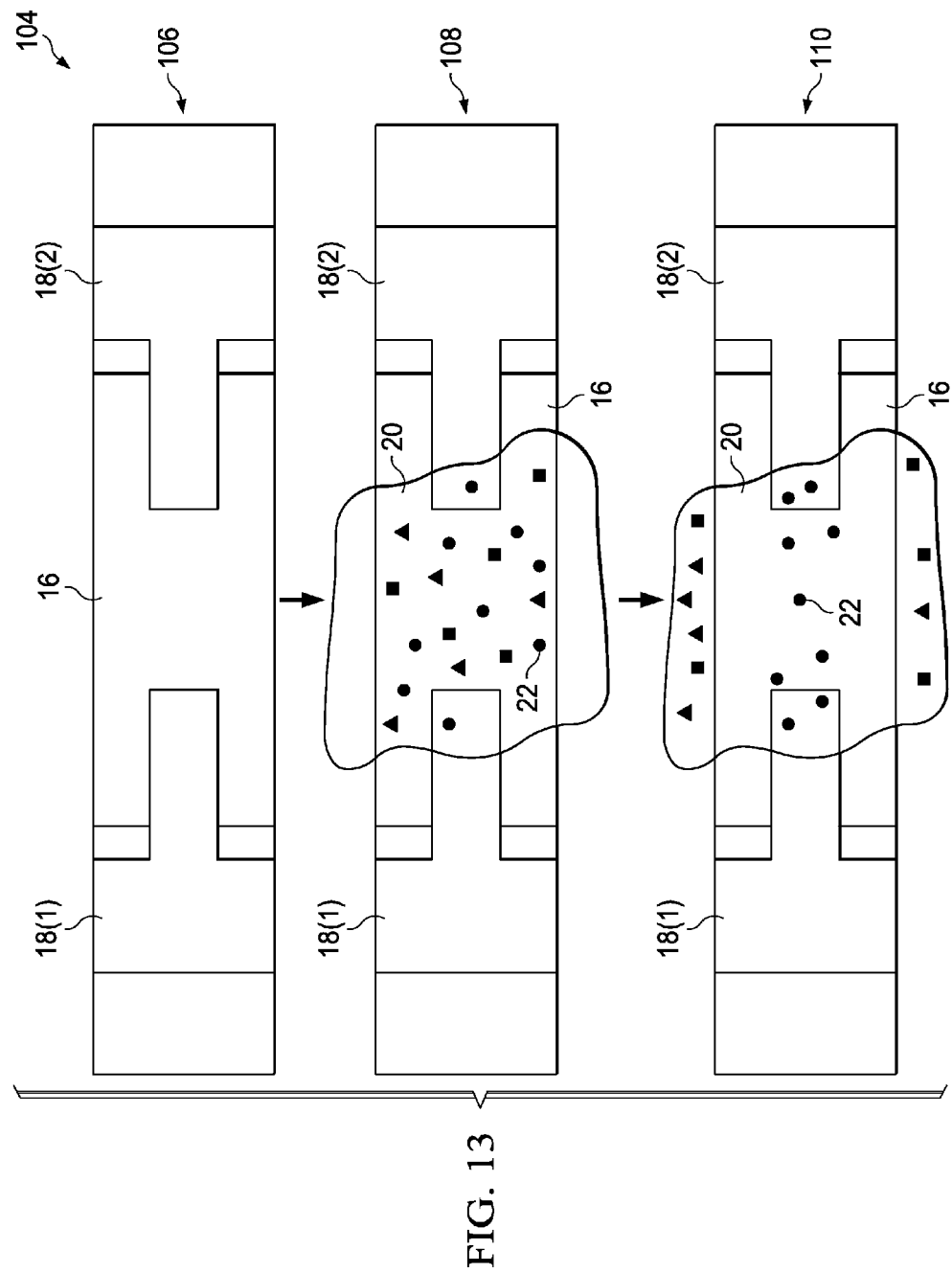
FIG. 13 is a simplified block diagram illustrating yet other example details of embodiments of the biosensing system.

Turning to FIG. 13, FIG. 13 is a simplified diagram illustrating example operations 104 associated with an embodiment of biosensing system 10. Use of ultra-low sample volumes (e.g., less than 100 microliters) can cause non-uniform distribution of analyte 22 at fluid-sensor interface 24, resulting in high noise and spurious artifacts in the measured output signal. In various embodiments, electrokinetic focusing may be used to direct charged or uncharged species of analyte 22 to a specific region of fluid-sensor interface 24 at sensing element 16, thereby reducing the non-uniform distribution of analyte 22. 'Electrokinetic focusing' as used in this Specification refers to using electrokinetic transport (e.g., electrophoretic migration of ions) to enable spatial confinement of fluid 20 and analyte 22 to fluid-sensor interface 24 at sensing element 16. Electrokinetic focusing can reduce detection time and enable the detection of charged and uncharged target species of analyte 22. In various embodiments, particle oscillation from gradient electric fields and dielectrophoresis (DEP) are used to effect electrokinetic focusing.

In some embodiments, a gradient electric field is applied transversely across electrodes 18(1) and 18(2) on the same (e.g., X-Y) plane. The gradient electric field causes local polarization of fluid 20 and target species of analyte 22, driving analyte 22 towards fluid-sensor interface 24 at sensing element 16. Under the influence of the gradient electric field, analyte 22 undergoes polarization (note that analyte 22 can be charged or uncharged prior to the application of the gradient electric field). The gradient electric field orthogonal to electrodes 18(1) and 18(2) within a microenvironment (e.g., a few 100 nm around each molecule of analyte 22) of analyte 22 causes polarization of analyte 22. The polarization and particle oscillation can be affected by the harmonic or resonance frequencies associated with the fluctuating gradient electric field. Such particle oscillation effects are compatible with single- and multi-phase sinusoidal voltage.

According to DEP, a force is exerted on any dielectric particle when it is subjected to a non-uniform electric field. In a general sense, all dielectric particles exhibit dielectrophoretic activity in the presence of electric fields; however, the strength of the force depends strongly on the medium and particles' electrical properties, on the particles' shape and size, and on the frequency of the electric field. Consequently, fields of a particular frequency can manipulate specific particles with relatively greater selectivity. DEP and particle oscillation are used to achieve targeted spreading of analyte 22 uniformly on sensing element 16.

At 106, a transverse voltage is applied across electrodes 18(1) and 18(2), causing a gradient electric field around them. At 108, a small volume (e.g., less than 1-10 microliters) of fluid 20 including analyte 22 is introduced on sensing element 16. In the absence of electrokinetic focusing, the movement of analyte 22 to fluid-sensor interface 24 at sensing element 16 is diffusion driven, which can be slow and non-uniform. At 110, under electrokinetic focusing based on particle oscillation from gradient electric fields and DEP, analyte 22 is spatially contained to a small, uniform region on sensing element 16, facilitating low noise measurements from biosensor 12. In some embodiments, electrokinetic focusing may be used together with impedance spectroscopy (e.g., measurement of dielectric properties of fluid 20 as a function of voltage frequency) to detect and measure analyte 22 in fluid 20 with biosensor 12.

Figure 14:
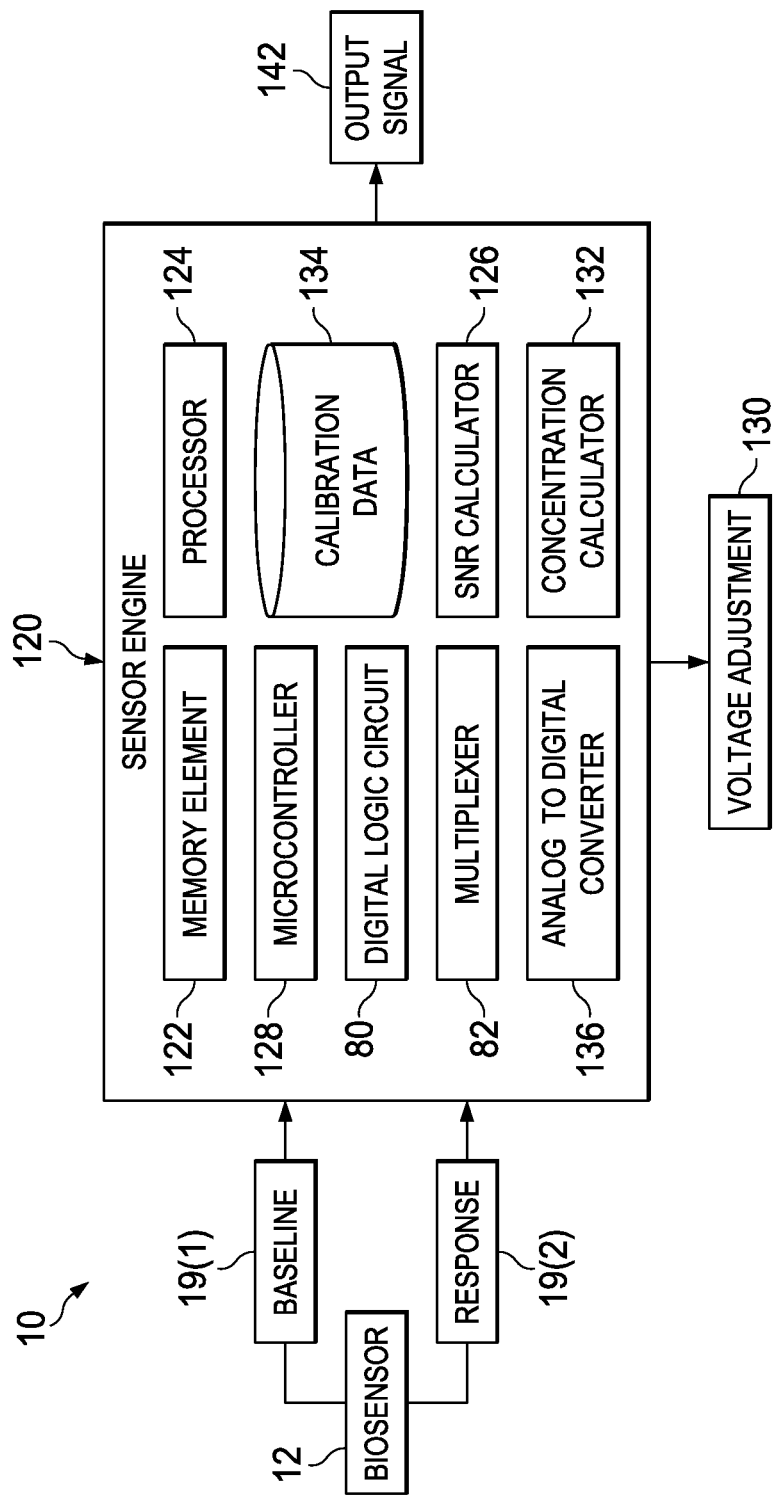
FIG. 14 is a simplified block diagram illustrating yet other example details of embodiments of the biosensing system.

Turning to FIG. 14, FIG. 14 is a simplified block diagram illustrating example details of biosensing system 10. Baseline 19(1) and response 19(2) from biosensor 12 may be fed to a sensor engine 120. Sensor engine 120 comprises a memory element 122 and a processor 124. A SNR calculator 126 in sensor engine 120 compares baseline 19(1) and response 19(2) and determines the SNR of the measurements. A microcontroller 128 may generate a voltage adjustment 130 to orthogonal voltage across orthogonal electrodes 18(1) and 18(3) to vary the SNR. Voltage adjustment is continued until a maximum SNR is achieved. A concentration calculator 132 may compare response 19(2) with stored calibration data 134 to estimate analyte concentration corresponding to measured response 19(2). In various embodiments, stored calibration data 134 can comprise calibration chart 39 of the foregoing figures. In some embodiments, the calculated analyte concentration may be verified and transmitted to an external device, such as a tethered wireless display.

An analog-to-digital converter (ADC) 136 in sensor engine 120 may digitize baseline 19(1) and response 19(2)

and feed the digital signals to digital circuit logic 80. In some embodiments, digitized response 19(2) may correspond to {T1, T2} of the foregoing figures and digitized baseline 19(1) may correspond to {O, B} of the foregoing figures. Digital circuit logic 80 may transform the digital signals to an output that is fed to multiplexer 82 in sensor engine 120. Multiplexer 82 may generate an output signal 142 depending on the values from digital circuit logic 80. Output signal 142 may light up an LED, or generate other suitable displays accordingly.

Figure 15:
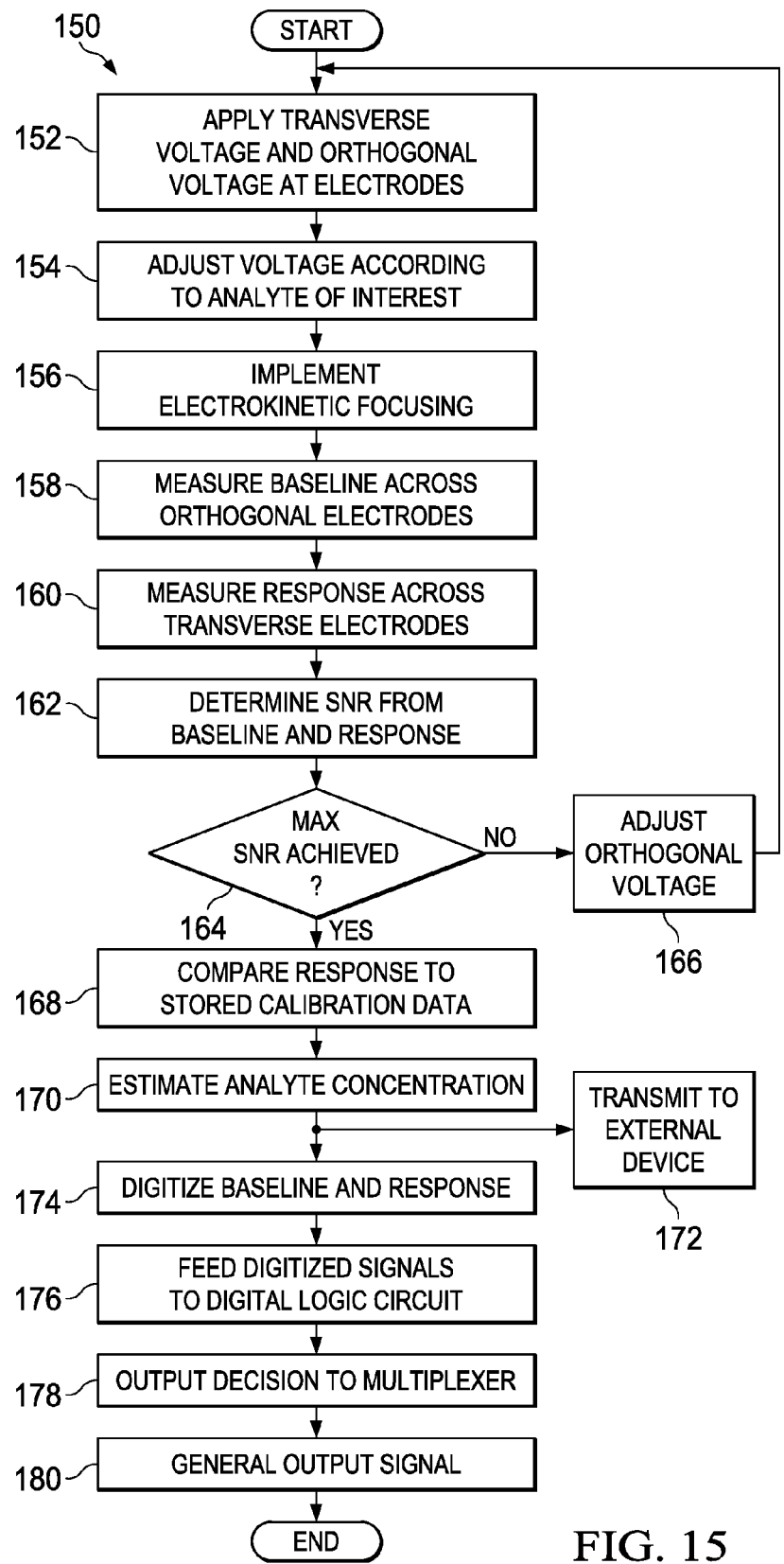
FIG. 15 is a simplified flow diagram illustrating example operations that may be associated with an embodiment of the biosensing system.

Turning to FIG. 15, FIG. 15 is a simplified flow diagram illustrating example operations 150 that may be associated with an embodiment of biosensing system 10. At 152, an input transverse voltage is applied to transverse electrodes 18(1) and 18(2) and an input orthogonal voltage is applied to orthogonal electrodes 18(1) and 18(3), the orthogonal voltage creating an electric field that is orthogonal to the electric field created by the transverse voltage. In some embodiments, the transverse voltage may comprise DC voltage, and the orthogonal voltage may comprise AC voltage. In some embodiments, instead of voltage, current may be applied across electrodes 18(1) and 18(3) to generate the transverse and orthogonal electric fields. In yet other embodiments, a steady state potential may be applied across electrodes 18(1) and 18(3) to general the transverse and orthogonal electric fields. In various embodiments, a microcontroller or microprocessor may be used to adjust a gain of biosensor 12. For example, a ratio of output signals to input voltage may be calculated to determine the gain of biosensor 12, with higher gain indicating higher sensitivity in some embodiments. The input voltages (or current, or steady state potential) may be adjusted accordingly to obtain better gain of biosensor 12.

At 154, voltage and frequency range of the AC voltage may be adjusted according to analyte 22 of interest in fluid 20. For example, sensitivity of biosensor 12 may be large for a particular target species at a specific combination of voltage amplitude and frequency of the AC voltage—in other words, biosensor 12 can detect small variations in concentrations of the particular target species at the specific combination of voltage amplitude and frequency of the AC voltage. The sensitivity may change if the target species changes, or the combination of voltage amplitude and frequency of the AC voltage changes. Conversely, biosensor 12 may detect a different target species with a different combination of voltage amplitude and frequency of the AC voltage. The sensitivity variation with voltage amplitude and frequency may be determined apriori; in some embodiments, biosensor 12 may be preconfigured to operate at a specific combination of voltage amplitude and frequency to detect a particular target species.

At 156, electrokinetic focusing may be optionally implemented through transverse electrodes 18(1) and 18(2), for example, adjusting the electric field generated by the transverse voltage to cause particle oscillation and dielectrophoretic effects on analyte 22 in fluid 20. At 158, baseline 19(1), for example, impedance, or capacitance, or current may be measured across orthogonal electrodes 18(1) and 18(3). At 160, response 19(2), for example, impedance, or capacitance, or current may be measured across transverse electrodes 18(1) and 18(2). At 162, response 19(2) may be compared to baseline 19(1) to determine the SNR of the measurements. In some embodiments, electrokinetic focusing may be performed after determining SNR; if the SNR is lower than a predetermined threshold, electrokinetic focusing may be performed, and otherwise, it may be neglected.

In some embodiments, tuning (e.g., adjusting) the height (e.g., thickness) of fluid-sensor interface 24 (e.g., Debye length tuning, EDL tuning) during electrokinetic focusing is achieved with orthogonal electrodes 18(1) and 18(3) (e.g., by varying a voltage, current, or steady state potential across electrodes 18(1) and 18(3) until a desired Debye length measurement is achieved). The height tuning enhances the target species attraction to fluid-sensor interface 24 and adds to the gradient electric field effect from transverse electrodes 18(1) and 18(2). At 164, a determination may be made whether maximum SNR is achieved. If not, the operations step to 166, at which the orthogonal voltage is adjusted and the operations repeated until maximum SNR is achieved.

At 168, response 19(2) is compared to stored calibration data 134. At 170, the analyte concentration is estimated based on calibration data 134. For example, calibration data 134 may comprise calibration chart 39. Response 19(2) may be plotted against various known analyte concentrations in calibration chart 39. A specific value of response 19(2) obtained at operation 160 may be plotted on calibration chart 39, and the corresponding analyte concentration estimated therefrom. At 172, the estimated analyte concentration may be verified and transmitted to an external end-user device, such as a computer, server, smartphone, display, etc.

Alternatively, or additionally, at 174, baseline 19(1) and response 19(2) may be digitized by ADC 136. At 176, the digitized signals may be fed to digital logic circuit 80. At 178, decisions output by digital logic circuit 80 may be fed to multiplexer 82. At 180, multiplexer 82 may generate output signal 142 depending on the input from digital circuit logic 80. Output signal 142 may light up an LED, or generate other suitable displays accordingly.

Figure 16:
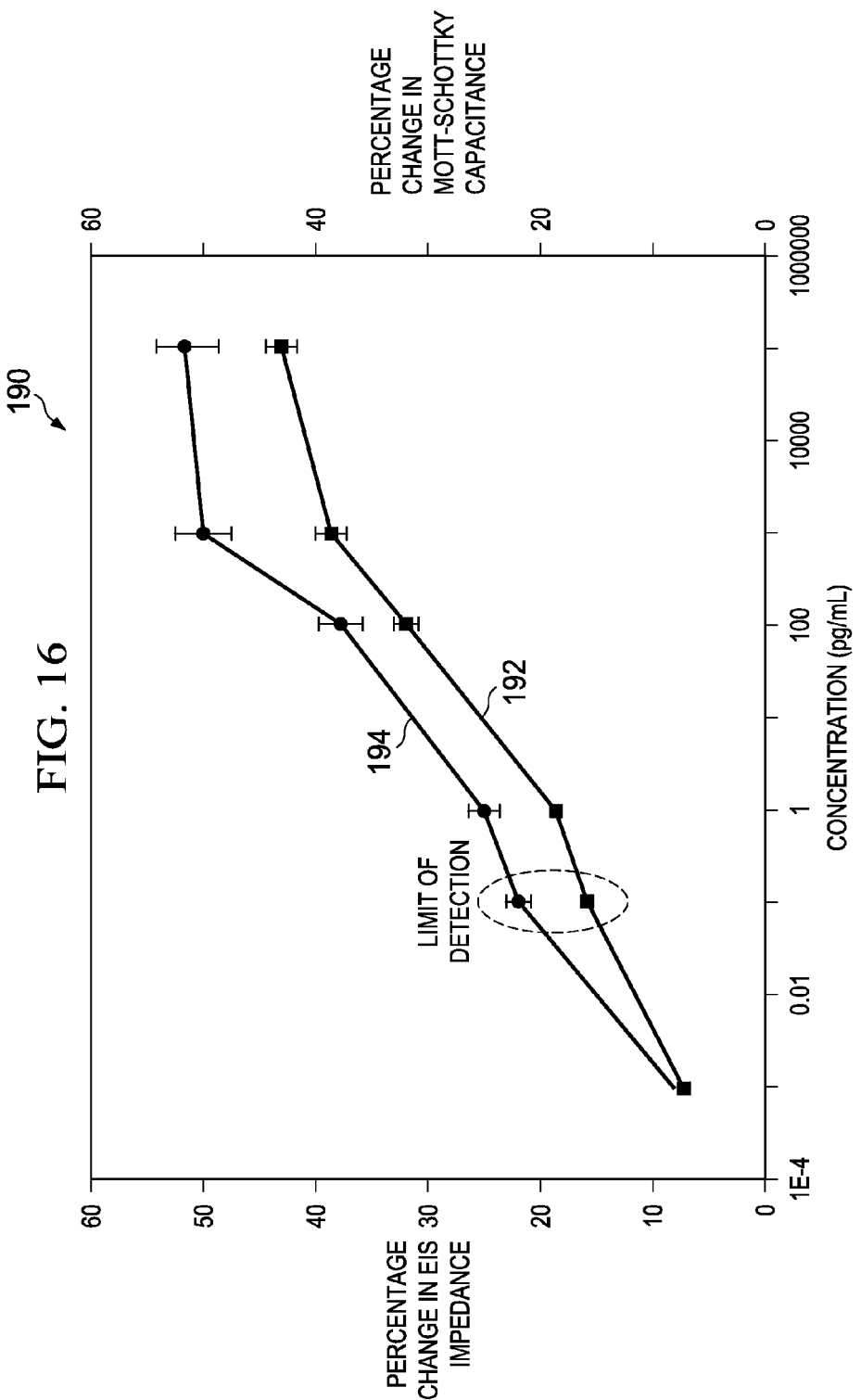
FIG. 16 is a simplified graph illustrating example details of an embodiment of the biosensing system.

Turning to FIG. 16, FIG. 16 is a simplified graph illustrating example details of biosensing system 10. An experiment to detect cardiac Troponin in human serum was conducted using biosensing system 10. Graph 190 illustrates a comparison of percentage change of impedance 192 using electrochemical impedance spectroscopy (EIS) methods and percentage change of capacitance 194 using Mott-Schottky analysis of capacitance-voltage measurements against analyte concentration along a common X-axis. EIS impedance represents the EDL characteristics formed in fluid 20 at the fluid-sensor interface 24. Mott-Schottky capacitance corresponds to a measure of electrical characteristics of the space charge region in sensing element 16.

With varying concentration of cardiac Troponin in fluid 20, a trend may be detected using percent change of EIS impedance 194 that is a result of binding of the capture probes 58 to surface of sensing element 16. Substantially simultaneously, the binding of capture probes 58 also results in work function modulation of the semiconductor material of sensing element 16 and changes the electrical characteristics (e.g., capacitance) of the space charge region (e.g., schematically shown in FIG. 8 as the bending of bands to achieve equilibrium). The trend of percent change to Mott-Schottky measured capacitance is similar to that of the percent change in EIS measured capacitance. Note that graph 190 can indicate a limit of detection (LoD) for each of plots 192 and 194. The LoD is the lowest analyte concentration likely to be reliably detected (e.g., distinguished, identified, etc) and at which detection is feasible.

Embodiments of biosensing system 10 described herein may be used in myriad applications. Note that the electron-ion mechanism of sensing may remain constant across the different applications, whereas linker molecules 56 and capture probes 58 for binding with analyte 22 may vary across the different applications. For example, some embodiments of biosensing system 10 may be used in skin-graft sensors. Portion 14B of substrate 14 may comprise a flexible, nanoporous membrane, which may be placed in direct contact with the skin and used for continuous, periodic monitoring of various molecules present in perspired sweat by the wearer. The information collected can be used to understand body response and behaviors, for example, to aid in disease diagnosis under various situations such as outpatient, inpatient, post-surgical etc.

In another example, some embodiments of biosensing system 10 may be used in smart catheters. Miniaturized catheters in microscale may be used for continuous drug delivery and in-vivo monitoring of injuries to blood vessels, tissues etc. Flexible, nanoporous biosensors as described herein can be integrated inside the catheters to perform biochemical detection, for example, to quantitatively study the molecular environment surrounding damaged, under-treatment tissue or blood vessel of interest. In addition, the microscale nature of biosensor 12 can enable analysis of inflation pressure, upstream blood pressure and downstream blood pressure.

In yet another example, some embodiments of biosensing system 10 may be used in smart tissue sensors. The sensor platform as described herein can be used for continuously monitoring tissue development and growth without interfering with the tissue itself. Patterned and controlled growth of semiconductor nanostructures arrays (such as ZnO) can be used to create conformal and biomimetic architectures that favor growth of tissue and other structural biological elements. Biosensor 12 can be integrated with semiconductor nanostructure arrays to continuously monitor the rate of growth, biochemical environment and the influence of catalysts on tissue development.

In yet another example, some embodiments of biosensing system 10 may be used in smart food sensors. Biosensor 12 as described herein can be used for real-time monitoring of packaged food quality. Various appropriate linker molecules 56 and capture probes 58 that bind with specific food breakdown byproducts released at very low concentrations may be used to estimate the quality of the packaged food. Some embodiments of biosensor 12 may be implemented in simple household food packages, which can include plastic covers and other sealable materials, as well as industrial grade food packaging processes.

In yet another example, some embodiments of biosensing system 10 may be used in bacterial sensors and/or smart bottles. The detection of bacterial quantity and type in water, milk, etc. can establish its safety and usability levels for consumption. Biosensor 12 described herein may be conjugated with nucleic acid vectors or capture probes 58 that can detect cyanobacteria, algae and other classes of bacteria that make the fluids unsafe for consumption. Biosensor 12 can be integrated onto a bottle used for collecting/storing the fluid (examples: water, milk, baby products, etc.) In yet another example, some embodiments of biosensing system 10 may be built on contact lens polymeric materials to detect biochemical markers in tears to quantitatively evaluating glaucoma and diabetes. In yet another example, some embodiments of biosensing system 10 may be used in a blood prick sensor for cancer detection, vascular disease detection, etc. In yet another example, some embodiments of biosensing system 10 may be used in urine testing strips for cancer detection. In yet another example, some embodiments of biosensing system 10 may be integrated into a mouth guard to test saliva for disease detection.

Note that only a few example applications are described herein; various other applications using integrated sensors within wearable or flexible fabric materials and other substrates may be included within the broad scope of the embodiments. Integrated sensors may also be envisioned within medical instruments such as catheters, probes, patches for non-communicable disease diagnosis such as cardiac, cancer, Alzheimer's, etc.

Some embodiments of biosensing system 10 as described herein provides rapid analyte detection and/or sensor devices and methods of use thereof in the identification of a binding event. Such methods find application in inter alia, immunoassays, screening assays, enzymatic assays, diagnostic assays, screening assays, assays for the identification of biological and/or environmental toxins, and others, as will be appreciated by one skilled in the art.

In various embodiments, nanostructures on the biosensor surface (e.g., surface of sensing element 16 proximate fluid-sensor interface 24) can be formed under controlled manufacturing conditions consistent with microchip scale and photomask processes, for example, to produce highly uniform and/or miniaturized and/or high-density array sensor devices. Biosensor 12 described herein may also be fabricated via microfabrication technology, or microtechnology, in one embodiment, applying the tools and processes of semiconductor fabrication to the formation of, for example, physical structures, such as electrodes 18(1)-18(3) and sensing element 16. Microfabrication technology allows for example, to precisely design features (e.g., wells, channels) with dimensions in the range of <1 mm to several centimeters on chips made, for example, of silicon, glass, or plastics. In some embodiments, NEMS or nanotechnology, for example, using nanoimprint lithography (NIL), may be used to construct the devices described herein.

According to various embodiments, biosensor 12 described herein may be adapted such that analysis of a species of interest may be conducted, in one embodiment, in biosensor 12 described herein, or in another embodiment, downstream of biosensor 12 described herein, for example, in a separate server coupled to the device. It is to be understood that the devices described herein may be useful in various analytical systems, including bioanalysis microsystems. Although the biosensor system has been described with respect to particular devices and methods, it will be understood that various changes and modifications can be made without departing from the scope of the embodiments.

Note that in this Specification, references to various features (e.g., elements, structures, modules, components, steps, operations, characteristics, etc.) included in "one embodiment", "example embodiment", "an embodiment", "another embodiment", "some embodiments", "various embodiments", "other embodiments", "alternative embodiment", and the like are intended to mean that any such features are included in one or more embodiments of the present disclosure, but may or may not necessarily be combined in the same embodiments. Furthermore, the words "optimize," "optimization," and related terms are terms of art that refer to improvements in speed and/or efficiency of a specified outcome and do not purport to indicate that a process for achieving the specified outcome has achieved, or is capable of achieving, an "optimal" or perfectly speedy/perfectly efficient state.

In example implementations, at least some portions of analyzing activities outlined herein may be implemented in software, for example, within sensor engine 120. In some embodiments, one or more of these features may be implemented in hardware, provided external to these elements, or consolidated in any appropriate manner to achieve the intended functionality. The various circuit elements may include software (or reciprocating software) that can coordinate in order to achieve the operations as outlined herein. In still other embodiments, these elements may include any suitable algorithms, hardware, software, components, modules, interfaces, or objects that facilitate the operations thereof.

In a general sense, the arrangements depicted in the FIGURES may be more logical in their representations, whereas a physical architecture may include various permutations, combinations, and/or hybrids of these elements. It is imperative to note that countless possible design configurations can be used to achieve the operational objectives outlined here. Accordingly, the associated infrastructure has a myriad of substitute arrangements, design choices, device possibilities, hardware configurations, software implementations, equipment options, etc.

In some of example embodiments, one or more memory elements (e.g., memory element 122) can store data used for the operations described herein. This includes the memory element being able to store instructions (e.g., software, logic, code, etc.) in non-transitory media, such that the instructions are executed to carry out the activities described in this Specification. A processor can execute any type of instructions associated with the data to achieve the operations detailed herein in this Specification. In one example, processors (e.g., processor 124, microcontroller 128) could transform an element or an article (e.g., data) from one state or thing to another state or thing. In another example, the activities outlined herein may be implemented with fixed logic or programmable logic (e.g., software/computer instructions executed by a processor) and the elements identified herein could be some type of a programmable processor, programmable digital logic (e.g., a field programmable gate array (FPGA), an erasable programmable read only memory (EPROM), an electrically erasable programmable read only memory (EEPROM)), an ASIC that includes digital logic, software, code, electronic instructions, flash memory, optical disks, CD-ROMs, DVD ROMs, magnetic or optical cards, other types of machine-readable mediums suitable for storing electronic instructions, or any suitable combination thereof.

These devices may further keep information in any suitable type of non-transitory storage medium (e.g., random access memory (RAM), read only memory (ROM), field programmable gate array (FPGA), erasable programmable read only memory (EPROM), electrically erasable programmable ROM (EEPROM), etc.), software, hardware, or in any other suitable component, device, element, or object where appropriate and based on particular needs. The information being tracked, sent, received, or stored in biosensing system 10 could be provided in any database, register, table, cache, queue, control list, or storage structure, based on particular needs and implementations, all of which could be referenced in any suitable timeframe. Any of the memory items discussed herein should be construed as being encompassed within the broad term 'memory element.' Similarly, any of the potential processing elements, modules, and machines described in this Specification should be construed as being encompassed within the broad term 'processor.'

It is also important to note that the operations and steps described with reference to the preceding FIGURES illustrate only some of the possible scenarios that may be executed by, or within, the system. Some of these operations may be deleted or removed where appropriate, or these steps may be modified or changed considerably without departing from the scope of the discussed concepts. In addition, the timing of these operations may be altered considerably and still achieve the results taught in this disclosure. The preceding operational flows have been offered for purposes of example and discussion. Substantial flexibility is provided by the system in that any suitable arrangements, chronologies, configurations, and timing mechanisms may be provided without departing from the teachings of the discussed concepts.

Although the present disclosure has been described in detail with reference to particular arrangements and configurations, these example configurations and arrangements may be changed significantly without departing from the scope of the present disclosure. For example, although the present disclosure has been described with reference to particular communication exchanges involving certain network access and protocols, biosensing system 10 may be applicable to other exchanges or routing protocols. Moreover, although biosensing system 10 has been illustrated with reference to particular elements and operations that facilitate the communication process, these elements, and operations may be replaced by any suitable architecture or process that achieves the intended functionality of biosensing system 10.

Numerous other changes, substitutions, variations, alterations, and modifications may be ascertained to one skilled in the art and it is intended that the present disclosure encompass all such changes, substitutions, variations, alterations, and modifications as falling within the scope of the appended claims. In order to assist the United States Patent and Trademark Office (USPTO) and, additionally, any readers of any patent issued on this application in interpreting the claims appended hereto, Applicant wishes to note that the Applicant: (a) does not intend any of the appended claims to invoke paragraph six (6) of 35 U.S.C. section 112 as it exists on the date of the filing hereof unless the words "means for" or "step for" are specifically used in the particular claims; and (b) does not intend, by any statement in the specification, to limit this disclosure in any way that is not otherwise reflected in the appended claims.

What is claimed is:
1. A biosensor, comprising:
a semiconductor sensing element;
a first conducting electrode and a second conducting electrode located on a first plane of the sensing element, wherein a first electric field is applied across the first electrode and the second electrode;
a third conducting electrode located on a second plane of the sensing element parallel to and removed from the first plane, wherein a second electric field is applied across the first electrode and the third electrode perpendicular to the first electric field; and
a dielectric substrate having a first portion adjacent a second portion, the first portion adjacent the sensing element and comprising pores, the first portion facilitating reception and containment of a fluid comprising an analyte on a surface of the sensing element distal from the third electrode, the surface defining an interface between the first portion and the sensing element, and the second portion facilitating dielectric separation of the fluid from the first electrode, the second electrode and the third electrode, wherein the mutually perpendicular first electric field and the second electric field facilitate adjusting a height of a fluid-sensor interface comprising an electrical double layer (EDL) in the fluid enabling detection and characterization of the analyte;
wherein the first portion of the substrate facilitates reception and containment of the fluid in the pores.

2. The biosensor of claim 1, wherein the first electric field is generated from direct current (DC) voltage applied across the first electrode and the second electrode, wherein the second electric field is generated from alternating current (AC) voltage applied across the first electrode and the third electrode.

3. The biosensor of claim 1, wherein the fluid-sensor interface further comprises a surface of the sensing element.

4. The biosensor of claim 3, wherein the fluid-sensor interface further comprises a layer of linker molecules bound to the surface of the sensing element.

5. The biosensor of claim 4, wherein the fluid-sensor interface further comprises a layer of capture probes bound to the layer of linker molecules.

6. The biosensor of claim 5, wherein the fluid-sensor interface further comprises blocking molecules bound to some of the linker molecules.

7. The biosensor of claim 1, wherein a first electrical response is measured across the first electrode and the third electrode, wherein a second electrical response is measured across the first electrode and the third electrode, wherein a comparison between the first electrical response and the second electrical response provides a measure of a signal-to-noise ratio (SNR) of the biosensor.

8. The biosensor of claim 7, wherein the first electric field is adjusted to change a Debye length of the EDL generated in the fluid, wherein the Debye length affects the SNR of the biosensor.

9. The biosensor of claim 7, wherein a concentration of the analyte is estimated from the second electrical response based on a calibration chart.

10. The biosensor of claim 1, wherein the first portion of the substrate comprises a porous, hydrophilic, biocompatible material, wherein the second portion of the substrate comprises a hydrophobic biocompatible material.

11. The biosensor of claim 1, wherein sensing element comprises a thin-film semiconductor, wherein the first electrode, the second electrode and the third electrode comprise nanostructures patterned on the thin-film sensing element.

12. The biosensor of claim 1, wherein the first electric field produces a gradient electric field facilitating electrokinetic focusing of the analyte on the sensing element.

13. The biosensor of claim 1, wherein the mutually perpendicular electric fields facilitate size and charge based detection and characterization of low concentrations of the analyte in a small volume of the fluid.

14. The biosensor of claim 1, wherein the biosensor is configured to be wearable, wherein the analyte is generated by the wearer, wherein the biosensor tests the analyte in-situ.

15. The biosensor of claim 1, wherein the analyte comprises a plurality of different target species in the fluid, wherein the biosensor enables separately detecting and characterizing each target species.

16. The biosensor of claim 1, further comprising a plurality of linker molecules residing on the surface within each of the pores.

\* \* \* \* \*